(12) United States Patent
Mueller et al.

(10) Patent No.: US 11,343,979 B2
(45) Date of Patent: *May 31, 2022

(54) PROCESS AND APPARATUS FOR PRODUCING MYCELIUM BIOMATERIAL

(71) Applicant: Ecovative Design LLC, Green Island, NY (US)

(72) Inventors: Peter James Mueller, Poestenkill, NY (US); Jacob Michael Winiski, Troy, NY (US); Meghan Anne O'Brien, Halfmoon, NY (US)

(73) Assignee: Ecovative Design LLC, Green Island, NY (US)

( * ) Notice: Subject to any disclaimer, the term of this patent is extended or adjusted under 35 U.S.C. 154(b) by 158 days.

This patent is subject to a terminal disclaimer.

(21) Appl. No.: 16/419,868

(22) Filed: May 22, 2019

(65) Prior Publication Data

US 2019/0357454 A1 Nov. 28, 2019

Related U.S. Application Data

(60) Provisional application No. 62/675,922, filed on May 24, 2018.

(51) Int. Cl.
*A01G 18/22* (2018.01)
*C12N 1/14* (2006.01)

(52) U.S. Cl.
CPC .............. *A01G 18/22* (2018.02); *C12N 1/14* (2013.01)

(58) Field of Classification Search
CPC ........ A01G 18/00; A01G 18/10; A01G 18/20; A01G 18/22; A01G 18/40; A01G 18/50
(Continued)

(56) References Cited

U.S. PATENT DOCUMENTS 1,979,176 A 10/1934 Schicht
2,509,984 A 5/1950 Morrow
(Continued)

FOREIGN PATENT DOCUMENTS

CN 1059662 A 3/1992
CN 1732887 A 2/2006
(Continued)

OTHER PUBLICATIONS

Agnese et al., "Investigating the Influence of Various Plasticizers on the Properties of Isolated Films of Polyvinyl Acetat". The 37th Annual meeting and Exposition of the Controlled Release Society, Jul. 2010, Portland, OR U.S.A.
(Continued)

*Primary Examiner* — David J Parsley
(74) *Attorney, Agent, or Firm* — Knobbe, Martens, Olson & Bear, LLP

(57) ABSTRACT

The process for producing mycelium biomaterial provides fresh oxygen to the growing mycelium biomaterial while removing waste heat and waste carbon dioxide by forced aeration through large volumes of material. In a first phase of fungal expansion, humidified air at a programmed temperature is passed upwardly and through a fungal inoculated substrate of discrete particles to allow the fungal inoculum to expand and dominate the substrate. Nutrient is added to the inoculated mixture and a second phase of fungal expansion is performed wherein humidified air at a programmed temperature is passed upwardly and through the nutrient enriched fungal inoculated substrate to allow the fungal inoculum to bond the discrete particles into a self-supporting biocomposite. The process and apparatus of the invention allows for the processing of grown materials bound by mycelium at depths of greater than 6" and particularly in the range of from 24" to 28".

15 Claims, 7 Drawing Sheets

(58) Field of Classification Search
USPC .......................................................... 47/1.1
See application file for complete search history.

(56) References Cited

U.S. PATENT DOCUMENTS

| | | | |
|---|---|---|---|
| 2,657,647 A | 11/1953 | Rapisarda | |
| 2,723,493 A | 11/1955 | Stoller | |
| 2,815,621 A | 12/1957 | Carter | |
| 2,964,070 A | 12/1960 | Linhardt | |
| 3,268,606 A | 8/1966 | Jaeger | |
| 3,316,592 A | 5/1967 | Forrest | |
| 3,317,375 A | 5/1967 | Molinet et al. | |
| 3,421,554 A | 1/1969 | Carter | |
| 3,477,558 A | 11/1969 | Fleischauer | |
| 3,499,261 A | 3/1970 | Hullhorst et al. | |
| 3,708,952 A | 1/1973 | Schulze et al. | |
| 3,717,953 A | 2/1973 | Kuhn et al. | |
| 3,782,033 A | 1/1974 | Hickerson | |
| 3,810,327 A | 5/1974 | Giansante | |
| 3,828,470 A | 8/1974 | Stoller | |
| 3,961,938 A | 6/1976 | Iizuka et al. | |
| 4,027,427 A | 6/1977 | Stoller et al. | |
| 4,036,122 A | 7/1977 | Langen | |
| 4,038,807 A | 8/1977 | Beardsley et al. | |
| 4,063,383 A | 12/1977 | Green | |
| 4,073,956 A | 2/1978 | Yates | |
| 4,127,965 A | 12/1978 | Mee | |
| 4,136,767 A | 1/1979 | Sarovich | |
| 4,226,330 A | 10/1980 | Butler | |
| 4,263,744 A * | 4/1981 | Stoller | C05F 17/936 47/1.1 |
| 4,265,915 A | 5/1981 | MacLennan et al. | |
| 4,294,929 A | 10/1981 | Solomons et al. | |
| 4,337,594 A | 7/1982 | Hanacek et al. | |
| 4,370,159 A | 1/1983 | Holtz | |
| 4,568,520 A | 2/1986 | Ackermann et al. | |
| 4,620,826 A | 11/1986 | Rubio et al. | |
| 4,716,712 A | 1/1988 | Gill | |
| 4,722,159 A | 2/1988 | Watanabe et al. | |
| 4,878,312 A | 11/1989 | Shimizu | |
| 4,922,650 A * | 5/1990 | Akao | A01G 18/22 47/1.1 |
| 4,960,413 A | 10/1990 | Sagar et al. | |
| 5,021,350 A | 6/1991 | Jung et al. | |
| 5,030,425 A | 7/1991 | Bowers-Irons et al. | |
| 5,074,959 A | 12/1991 | Yamanaka et al. | |
| 5,085,998 A | 2/1992 | Lebron et al. | |
| 5,088,860 A | 2/1992 | Stockdale et al. | |
| 5,123,203 A | 6/1992 | Hiromoto | |
| 5,230,430 A | 7/1993 | Kidder | |
| 5,306,550 A | 4/1994 | Nishiyama et al. | |
| 5,335,770 A | 8/1994 | Baker et al. | |
| 5,370,714 A | 12/1994 | Ogawa | |
| 5,433,061 A | 7/1995 | Hutchinson et al. | |
| 5,440,860 A | 8/1995 | Meli et al. | |
| 5,475,479 A | 12/1995 | Hatakeyama et al. | |
| 5,498,384 A | 3/1996 | Volk et al. | |
| 5,503,647 A | 4/1996 | Dahlberg et al. | |
| 5,511,358 A | 4/1996 | Morita et al. | |
| 5,532,217 A | 7/1996 | Silver et al. | |
| 5,569,426 A | 10/1996 | Le Blanc | |
| 5,589,390 A | 12/1996 | Higuchi et al. | |
| 5,590,489 A | 1/1997 | Hattori et al. | |
| 5,598,876 A | 2/1997 | Zanini et al. | |
| 5,606,836 A | 3/1997 | Insalaco et al. | |
| 5,647,180 A | 7/1997 | Billings et al. | |
| 5,681,738 A | 10/1997 | Beelman et al. | |
| 5,682,929 A | 11/1997 | Maginot et al. | |
| 5,685,124 A | 11/1997 | Jandl | |
| 5,711,353 A | 1/1998 | Ichikawa et al. | |
| 5,802,763 A | 9/1998 | Milstein | |
| 5,854,056 A | 12/1998 | Dschida | |
| 5,888,803 A | 3/1999 | Starkey | |
| 5,897,887 A | 4/1999 | Haeberli | |
| 5,919,507 A | 6/1999 | Beelman et al. | |
| 5,944,928 A | 8/1999 | Seidner | |
| 5,948,674 A | 9/1999 | Mankiewicz | |
| 5,979,109 A | 11/1999 | Sartor et al. | |
| 6,041,544 A | 3/2000 | Kananen et al. | |
| 6,041,835 A | 3/2000 | Price | |
| 6,098,677 A | 8/2000 | Wegman et al. | |
| 6,112,504 A | 9/2000 | McGregor et al. | |
| 6,197,573 B1 | 3/2001 | Suryanarayan et al. | |
| 6,226,962 B1 | 5/2001 | Eason et al. | |
| 6,300,315 B1 | 10/2001 | Liu | |
| 6,306,921 B1 | 10/2001 | Al Ghatta et al. | |
| 6,329,185 B1 | 12/2001 | Kofod et al. | |
| 6,349,988 B1 | 2/2002 | Foster et al. | |
| 6,402,953 B1 | 6/2002 | Gorovoj et al. | |
| 6,425,714 B1 | 7/2002 | Waddell | |
| 6,444,437 B1 | 9/2002 | Sporleder et al. | |
| 6,471,993 B1 | 10/2002 | Shastri et al. | |
| 6,475,811 B1 | 11/2002 | Babcock | |
| 6,482,942 B1 | 11/2002 | Vittori | |
| 6,491,480 B2 | 12/2002 | Waddell | |
| 6,500,476 B1 | 12/2002 | Martin et al. | |
| 6,523,721 B1 | 2/2003 | Nomoto et al. | |
| 6,603,054 B2 | 8/2003 | Chen et al. | |
| 6,620,614 B1 | 9/2003 | Luth et al. | |
| 6,660,164 B1 | 12/2003 | Stover | |
| 6,679,301 B2 | 1/2004 | Makino et al. | |
| 6,726,911 B1 | 4/2004 | Jülich et al. | |
| 7,043,874 B2 | 5/2006 | Wasser et al. | |
| 7,073,306 B1 | 7/2006 | Hagaman | |
| 7,122,176 B2 | 10/2006 | Stamets | |
| 7,179,356 B2 | 2/2007 | Aksay et al. | |
| 7,395,643 B2 | 7/2008 | Franchini et al. | |
| 7,514,248 B2 | 4/2009 | Gower et al. | |
| 7,573,031 B2 | 8/2009 | Behar et al. | |
| 7,621,300 B2 | 11/2009 | Bonney et al. | |
| 7,661,248 B2 | 2/2010 | Conti et al. | |
| 7,754,653 B2 | 7/2010 | Hintz | |
| 7,836,921 B2 | 11/2010 | Isomura et al. | |
| 8,001,719 B2 | 8/2011 | Bayer et al. | |
| 8,205,646 B2 | 6/2012 | Isomura et al. | |
| 8,227,224 B2 | 7/2012 | Kalisz et al. | |
| 8,227,233 B2 | 7/2012 | Kalisz et al. | |
| 8,241,415 B2 | 8/2012 | Wantling et al. | |
| 8,298,810 B2 | 10/2012 | Rocco et al. | |
| 8,313,939 B2 | 11/2012 | Kalisz et al. | |
| 8,517,064 B2 | 8/2013 | Isomura et al. | |
| 8,658,407 B2 | 2/2014 | Lyons et al. | |
| 8,763,653 B2 | 7/2014 | Weigel et al. | |
| 8,999,687 B2 | 4/2015 | Bayer et al. | |
| 9,079,978 B2 | 7/2015 | Räsänen et al. | |
| 9,085,763 B2 | 7/2015 | Winiski et al. | |
| 9,253,889 B2 | 2/2016 | Bayer et al. | |
| 9,332,779 B2 | 5/2016 | Marga | |
| 9,394,512 B2 | 7/2016 | Bayer et al. | |
| 9,469,838 B2 | 10/2016 | Schaak et al. | |
| 9,485,917 B2 | 11/2016 | Bayer et al. | |
| 9,555,395 B2 | 1/2017 | Araldi et al. | |
| 9,714,180 B2 | 7/2017 | McIntyre et al. | |
| 9,752,122 B2 | 9/2017 | Marga et al. | |
| 9,795,088 B2 | 10/2017 | Bayer et al. | |
| 9,801,345 B2 | 10/2017 | Bayer et al. | |
| 9,803,171 B2 | 10/2017 | Bayer et al. | |
| 9,879,219 B2 | 1/2018 | McIntyre et al. | |
| 9,914,906 B2 | 3/2018 | Winiski et al. | |
| 10,125,347 B2 | 11/2018 | Winiski | |
| 10,144,149 B2 | 12/2018 | Araldi et al. | |
| 10,154,627 B2 | 12/2018 | McIntyre et al. | |
| 10,172,301 B2 | 1/2019 | McNamara et al. | |
| 10,266,695 B2 | 4/2019 | Lucht et al. | |
| 10,407,675 B2 | 9/2019 | Bayer et al. | |
| 10,525,662 B2 | 1/2020 | Bayer et al. | |
| 10,537,070 B2 | 1/2020 | Betts et al. | |
| 10,583,626 B2 | 3/2020 | Bayer et al. | |
| 10,589,489 B2 | 3/2020 | Bayer et al. | |
| 10,687,482 B2 | 6/2020 | Ross et al. | |
| 10,785,925 B2 | 9/2020 | McNamara et al. | |
| 2001/0012235 A1 | 8/2001 | Schuchardt | |
| 2002/0110427 A1 | 8/2002 | Waddell | |
| 2002/0131828 A1 | 9/2002 | Waddell | |

(56) References Cited

U.S. PATENT DOCUMENTS

| | | |
|---|---|---|
| 2002/0131933 A1 | 9/2002 | Delmotte |
| 2003/0017565 A1 | 1/2003 | Echigo et al. |
| 2003/0056451 A1 | 3/2003 | Pisek et al. |
| 2003/0121201 A1 | 7/2003 | Dahlberg et al. |
| 2003/0232895 A1 | 12/2003 | Omidian et al. |
| 2004/0000090 A1 | 1/2004 | Miller |
| 2004/0020553 A1 | 2/2004 | Amano |
| 2004/0166576 A1 | 8/2004 | Sadaie |
| 2004/0177585 A1 | 9/2004 | Vermette |
| 2005/0133536 A1 | 6/2005 | Kelsey et al. |
| 2005/0137272 A1 | 6/2005 | Gaserod et al. |
| 2006/0134265 A1 | 6/2006 | Beukes |
| 2006/0280753 A1 | 12/2006 | McNeary |
| 2007/0079944 A1 | 4/2007 | Amidon et al. |
| 2007/0196509 A1 | 8/2007 | Riman et al. |
| 2007/0225328 A1 | 9/2007 | Fritz et al. |
| 2007/0227063 A1 | 10/2007 | Dale et al. |
| 2007/0294939 A1 | 12/2007 | Spear et al. |
| 2008/0017272 A1 | 1/2008 | Isomura et al. |
| 2008/0046277 A1 | 2/2008 | Stamets |
| 2008/0047966 A1 | 2/2008 | Carson |
| 2008/0145577 A1 | 6/2008 | Bayer et al. |
| 2008/0234210 A1 | 9/2008 | Rijn et al. |
| 2008/0295399 A1 | 12/2008 | Kawai et al. |
| 2008/0296295 A1 | 12/2008 | Kords et al. |
| 2009/0107040 A1 | 4/2009 | Vandnhove |
| 2009/0191289 A1 | 7/2009 | Lutz et al. |
| 2009/0241623 A1 | 10/2009 | Matano et al. |
| 2009/0246467 A1 | 10/2009 | Delantar |
| 2009/0272758 A1 | 11/2009 | Karwacki et al. |
| 2009/0307969 A1 | 12/2009 | Bayer et al. |
| 2009/0321975 A1 | 12/2009 | Schlummer |
| 2010/0101190 A1 | 4/2010 | Dillon |
| 2010/0158976 A1 | 6/2010 | O'Brien et al. |
| 2010/0159509 A1 | 6/2010 | Xu et al. |
| 2010/0199601 A1 | 8/2010 | Boldrini et al. |
| 2010/0227931 A1 | 9/2010 | Kuwano et al. |
| 2010/0243135 A1 | 9/2010 | Pepper et al. |
| 2010/0326564 A1 | 12/2010 | Isomura et al. |
| 2011/0094154 A1 | 4/2011 | Joaquin |
| 2011/0108158 A1 | 5/2011 | Huwiler et al. |
| 2011/0265688 A1 | 11/2011 | Kalisz et al. |
| 2011/0268980 A1 | 11/2011 | Kalisz et al. |
| 2011/0269209 A1 | 11/2011 | Rocco et al. |
| 2011/0269214 A1 | 11/2011 | Kalisz et al. |
| 2011/0306107 A1 | 12/2011 | Kalisz et al. |
| 2012/0000165 A1 | 1/2012 | Williams |
| 2012/0006446 A1 | 1/2012 | Isomura et al. |
| 2012/0060446 A1 | 3/2012 | Merz |
| 2012/0076895 A1 | 3/2012 | Kirejevas et al. |
| 2012/0115199 A1 | 5/2012 | Li et al. |
| 2012/0132314 A1 | 5/2012 | Weigel et al. |
| 2012/0135504 A1 | 5/2012 | Ross |
| 2012/0225471 A1 | 9/2012 | McIntyre et al. |
| 2012/0227899 A1 | 9/2012 | McIntyre et al. |
| 2012/0231140 A1 | 9/2012 | Hofmann et al. |
| 2012/0270031 A1 | 10/2012 | Guan et al. |
| 2012/0270302 A1 | 10/2012 | Bayer et al. |
| 2012/0315687 A1 | 12/2012 | Bayer et al. |
| 2013/0095560 A1 | 4/2013 | McIntyre et al. |
| 2013/0105036 A1 | 5/2013 | Smith et al. |
| 2013/0210327 A1 | 8/2013 | Corominas |
| 2013/0224840 A1 | 8/2013 | Bayer et al. |
| 2013/0274892 A1 | 10/2013 | Lelkes et al. |
| 2013/0309755 A1 | 11/2013 | McIntyre et al. |
| 2014/0038619 A1 | 2/2014 | Moulsley |
| 2014/0056653 A1 | 2/2014 | Scully et al. |
| 2014/0069004 A1 | 3/2014 | Bayer et al. |
| 2014/0093618 A1 | 4/2014 | Forgacs et al. |
| 2014/0163142 A1 | 6/2014 | Zhang et al. |
| 2014/0173977 A1 | 6/2014 | Juscius |
| 2014/0186927 A1 | 7/2014 | Winiski et al. |
| 2014/0371352 A1 | 12/2014 | Dantin et al. |
| 2015/0033620 A1 | 2/2015 | Greetham et al. |
| 2015/0038619 A1 | 2/2015 | McIntyre et al. |
| 2015/0101509 A1 | 4/2015 | McIntyre et al. |
| 2015/0197358 A1 | 7/2015 | Larsen |
| 2015/0342138 A1 | 12/2015 | Bayer et al. |
| 2015/0342224 A1 | 12/2015 | Medoff |
| 2016/0002589 A1 | 1/2016 | Winiski |
| 2016/0264926 A1 | 9/2016 | Winiski et al. |
| 2016/0355779 A1 | 12/2016 | Ross |
| 2017/0000040 A1 | 1/2017 | Bayer et al. |
| 2017/0028600 A1 | 2/2017 | McIntyre et al. |
| 2017/0071214 A1 | 3/2017 | Rehage |
| 2017/0218327 A1 | 8/2017 | Amstislavski et al. |
| 2017/0253849 A1 | 9/2017 | Miller et al. |
| 2017/0253852 A1 | 9/2017 | Bayer et al. |
| 2018/0014468 A1 | 1/2018 | Ross et al. |
| 2018/0148682 A1 | 5/2018 | Ross et al. |
| 2018/0282529 A1 | 10/2018 | Kaplan-Bie |
| 2018/0368337 A1 | 12/2018 | McIntyre et al. |
| 2019/0059431 A1 | 2/2019 | Kozubal et al. |
| 2019/0090436 A1 | 3/2019 | Betts et al. |
| 2019/0284307 A1 | 9/2019 | Chase et al. |
| 2019/0322997 A1 | 10/2019 | Schaak |
| 2019/0330668 A1 | 10/2019 | Kozubal et al. |
| 2019/0338240 A1 | 11/2019 | Carlton et al. |
| 2019/0359931 A1 | 11/2019 | Mueller et al. |
| 2019/0390156 A1 | 12/2019 | Bayer et al. |
| 2020/0024577 A1 | 1/2020 | Carlton et al. |
| 2020/0025672 A1 | 1/2020 | Scullin et al. |
| 2020/0055274 A1 | 2/2020 | Bayer et al. |
| 2020/0095535 A1 | 3/2020 | Kozubal et al. |
| 2020/0102530 A1 | 4/2020 | Winiski et al. |
| 2020/0146224 A1 | 5/2020 | Kaplan-Bie et al. |
| 2020/0157506 A1 | 5/2020 | Bayer et al. |
| 2020/0208097 A1 | 7/2020 | Winiski |
| 2020/0239830 A1 | 7/2020 | O'Brien et al. |
| 2020/0268031 A1 | 8/2020 | Macur et al. |
| 2020/0270559 A1 | 8/2020 | Macur et al. |
| 2020/0392341 A1 | 12/2020 | Smith et al. |
| 2021/0127601 A9 | 5/2021 | Kaplan-Bie et al. |
| 2021/0317433 A9 | 10/2021 | Schaak |
| 2021/0348117 A9 | 11/2021 | Winiski |

FOREIGN PATENT DOCUMENTS

| | | |
|---|---|---|
| CN | 101248869 A | 8/2008 |
| CN | 101653081 A | 2/2010 |
| CN | 106947702 A | 7/2017 |
| EP | 0226292 A1 | 6/1987 |
| EP | 1312547 A1 | 5/2003 |
| EP | 2677030 A1 | 12/2013 |
| EP | 2735318 A1 | 5/2014 |
| EP | 2875805 A1 | 5/2015 |
| EP | 2878340 A1 | 6/2015 |
| EP | 2485779 B1 | 2/2018 |
| EP | 3292769 A1 | 3/2018 |
| GB | 142800 A | 1/1921 |
| GB | 1525484 A | 9/1978 |
| GB | 2032456 A | 5/1980 |
| GB | 2165865 A | 4/1986 |
| IN | 358266 B | 7/2020 |
| JP | H03234889 A | 10/1991 |
| JP | H049316 A | 1/1992 |
| JP | 6111510 B1 | 4/2017 |
| KR | 20050001175 A | 1/2005 |
| KR | 101851655 B1 | 4/2018 |
| WO | WO 1999/024555 | 5/1999 |
| WO | WO 2001/087045 | 11/2001 |
| WO | WO 2005/067977 | 7/2005 |
| WO | WO 2008/025122 | 3/2008 |
| WO | WO 2008/073489 | 6/2008 |
| WO | WO 2010/005476 | 1/2010 |
| WO | WO 2012/122092 | 9/2012 |
| WO | WO 2014/039938 | 3/2014 |
| WO | WO 2014/195641 | 12/2014 |
| WO | WO 2016/149002 | 9/2016 |
| WO | WO 2017/056059 | 4/2017 |
| WO | WO 2017/120342 | 7/2017 |
| WO | WO 2017/136950 | 8/2017 |
| WO | WO 2017/151684 | 9/2017 |
| WO | WO 2017/205750 | 11/2017 |

(56) References Cited

FOREIGN PATENT DOCUMENTS

| | | |
|---|---|---|
| WO | WO 2018/011805 | 1/2018 |
| WO | WO 2018/014004 | 1/2018 |
| WO | WO 2018/064968 | 4/2018 |
| WO | WO 2018/183735 | 10/2018 |
| WO | WO 2018/189738 | 10/2018 |
| WO | WO 2019/046480 | 3/2019 |
| WO | WO 2019/099474 | 5/2019 |
| WO | WO 2019/178406 | 9/2019 |
| WO | WO 2019/217175 | 11/2019 |
| WO | WO 2019/226823 | 11/2019 |
| WO | WO 2019/246636 | 12/2019 |
| WO | WO 2020/023450 | 1/2020 |
| WO | WO 2020/072140 | 4/2020 |
| WO | WO 2020/082043 | 4/2020 |
| WO | WO 2020/082044 | 4/2020 |
| WO | WO 2020/102552 | 5/2020 |
| WO | WO 2020/106743 | 5/2020 |
| WO | WO 2020/176758 | 9/2020 |
| WO | WO 2020/186068 | 9/2020 |
| WO | WO 2020/186169 | 9/2020 |
| WO | WO 2020/237201 | 11/2020 |

OTHER PUBLICATIONS

Amsellem et al., "Long-term preservation of viable mycelia of two mycoherbicidal organisms". Crop Protection (1999) 18: 643-649.

Angelini et al., "Effect of antimicrobial activity of Melaleuca alternifolia essential oil on antagonistic potential of *Pleurotus* species against Trichoderma harzianum in dual culture." World J Microbiol Biotech. (2008) 24(2): 197-202.

Antón et al., "PimM, a PAS Domain Positive Regulator of Pimaricin Biosynthesis in Streptomyces natalensis." Microbiol. (2007) 153: 3174-3183.

Appels et al., "Hydrophobin gene deletion and environmental growth conditions impact mechanical properties of mycelium by affecting the density of the material." Scientific Reports (2018) 8(1): 1-7.

Arshad et al., "Tissue engineering approaches to develop cultured meat from cells: a mini review." Cogent Food & Agriculture (2017) 3(1): 1320814 in 11 pages.

Ashiuchi et al., "Isolation of Bacillus subtilis (chungkookjang), a poly-gamma-glutamate producer with high genetic competence". Appl Microbiol Biotechnol. (2011) 57: 764-769.

Bajaj et al., "Poly (glutamic acid)—An emerging biopolymer of commercial interest". Bioresource Tech. (2011) 102(10): 5551-5561.

Baysal et al., "Cultivation of oyster mushroom on waste paper with some added supplementary materials". Biosource Technology (2003) 89: 95-97.

Begum et al., "Bioconversion and saccharification of some lignocellulosic wastes by Aspergillus oryzae ITCC-4857.01 for fermentable sugar production". Elect J Biotech. (2011) (14)5: 3 in 8 pages.

Belardinelli et al., "Actions of Adenosine and Isoproterenol on Isolated Mammalian Ventricular Myocytes." Circulation Res. (1983) 53(3): 287-297.

Belay et al., "Preparation and Characterization of Graphene-agar and Graphene Oxide-agar Composites." JOAPS (2017) 134(33): 45085.

Binder et al., "Phylogenetic and phylogenomic overview of the Polyporales". Mycologia (Nov.-Dec. 2013) 105(6): 1350-1373.

Blanchette et al., "Fungal mycelial mats used as textile by indigenous people of North America", Mycologia (Feb. 20, 2021) pp. 1-7.

Booth et al., "Potential of a dried mycelium formulation of an indigenous strain of Metarhizium anisopliae against subterranean pests of cranberry." Biocontrol Science and Technology (2000) 10: 659-668.

Bormann et al., "Characterization of a Novel, Antifungal, Chitin-binding Protein from Streptomyces Tendae Tü901 that Interferes with Growth Polarity." J Bacter. (1999) 181(24): 7421-7429.

Bowman et al., "The structure and synthesis of the fungal cell wall". Bioassays (2006) 28(8): 799-808.

Bružauskaite et al., "Scaffolds and Cells for Tissue Regernation: Different Scaffold Pore Sizes—Different Cell Effects." Cytotechnology (2016) 68(3): 355-369.

Byrd, "Clean meat's path to your dinner plate", The Good Food Institute, website accessed Nov. 14, 2018, https://www.gfi.org/clean-meats-path-to-commercialization; 11 pages.

Cerimi et al., "Fungi as source for new bio-based materials: a patent review", Fungal Biol Biotechnol. (2019) 6: 17; 10 pgs.

Chai et al., "β-Glucan Synthase Gene Overexpression and β-Glucans Overproduction in Pleurotus ostreatus Using Promoter Swapping". PLoS ONE (2013) 8(4): e61693 in 7 pages.

Chaudhary et al., "Understanding rice hull ash as fillers in polymers: a review". Silicon Chemistry (2002) 1:281-289.

Chi et al., "Can Co-culturing of Two White-rot Fungi Increase Lignin Degradation and the Production of Lignin-degrading Enzymes?" Inter'l Biodeter Biodegrad. (2007) 59(1): 32-39.

Collins English Dictionary, "Mould", retrieved from http://collinsdictionary.com/dictionary/english/mould, archived on Apr. 8, 2015, 3 pages.

Dias et al., "Synthesis and characterization of chitosan-polyvinyl alcohol-bioactive glass hybrid membranes". Biomatter (2011) 1(1): 114-119.

Elleuche et. al., "Carbonic anhydrases in fungi". Microbiology (2010) 156: 23-29.

Elsacker et al., "Growing living and multifunctional mycelium composites for large-scale formwork applications using robotic abrasive wire-cutting", Construction Bldg Mater. (2021) 283: 122732 in 16 pages.

Fleet G.H., "Cell walls", in The Yeasts, by Rose et al. [Eds.] 2nd Edition. vol. 4. London: Academic Press. (1991) pp. 199-277.

Frandsen R.J.N., "A guide to binary vectors and strategies for targeted genome modification in fungi using Agrobacterium tumefaciens-mediated transformation". J Microbiol Methods (2011) 87: 247-262.

Gardening KnowHow, Perlite Soil Info: Learn About Perlite Potting Soil, online at www.gardeningknowhow.com/garden-how-to/soil-fertilizers/perlite-potting-soil.htm downloaded on Dec. 16, 2015., 3 pages.

Glowacki et al., "Bioconjugation of Hydrogen-bonded Organic Semiconductors with Functional Proteins." J Mate Chem. C (2015) 3(25): 6554-6564.

Goodell et al., "Fungal Decay of Wood: Soft Rot-Brown Rot-white Rot". In Development of Commercial Wood Preservatives; Schultz et al. [Ed.] ACS Symposium Series; American Chemical Society, Washington, D.C. (2008), Chapter 2, pp. 9-31.

Google Report, Complete colonization substrate mushroom (2 pages) Jan. 30, 2018., 2 pages.

Google Dictionary Definition "Composite", downloaded on Nov. 21, 2018; 1 page.

Gourmet Mushroom, Inc., "What is Mushroom?"—Mushroom Facts Mushroom Information—Educational & Science Projects (2004). Downloaded from www.gmushrooms.com, on Nov. 27, 2017; 5 pages.

Grant, James. J.—"An investigation of the airflow in mushroom growing structures, the development of an improved, three-dimensional solution technique for fluid flow and its evaluation for the modelling of mushroom growing structures", Doctoral Thesis Sep. 2002; 326 pages.

Greetham et al., "Pheotypic characterisation of *Saccharomyces sensu* stricto to Inhibitory Compounds Released During the Deconstruction of Lignocellulosic Material." 3th International Congress on Yeasts, ICY 2012, Aug. 26-30, Madison, USA; 1 page.

Griffin et al., "Regulation of macromolecular synthesis, colony development and specific growth rate of Achlya bisexualis during balanced growth". J General Microbiol. (1974) 80(2): 381-388.

Growers Supply. "Horticultural Coarse Perlite—4 Cubic Fee—Growers Supply". URL: https://growerssupply.com; Growers Supply 2012; www.growerssupply.com/farm/supplies/prod1:gs_growing_mediums:pg111049.html; downloaded Dec. 14, 2020 in 3 pages.

(56) References Cited

OTHER PUBLICATIONS

Haneef et al., "Advanced Materials from Fungal Mycelium: Fabrication and Tuning of Physical Properties", Scientific Reports 7(1): 1-11; DOI: 10.1038/srep41292, Jan. 24, 2017.
Heinzkill et al., "Characterization of laccases and peroxidases from wood-rotting fungi (family Coprinaceae)." Appl Environ Microbiol. (1998) 64: 1601-1606.
Heisig et al., USGS, "Ground-Water Resources of the Clifton Park Area, Saratoga County, New York", 2002, retrieved from the internet (Oct. 15, 2016): http://ny.water.usgs.gov/pubs/wri/wri014104/wrir01-4104.pdf; 27 pages.
Home Depot "Miracle Gro® Perlite Mix", retrieved from the internet: http://homedepot.com/p/Miracle-Gro-8-pt-Perlite-Mix-74278430/204502291; 2 pages.
Home Depot "Pennington—Fast Acting Gypsum", retrieved from the internet: http://homedepot.com/p/Miracle-Gro-8-pt-Perlite-Mix-74278430/204502291; 2 pages.
Horton et al., "Regulation of Dikaryon-Expressed Genes by FRT1 in the Basidiomycete Schizophyllum commune". Fungal Genet Biol. (1999) 26(1): 33-47.
Howden et al., "The effects of breathing 5% CO2 on human cardiovascular responses and tolerance to orthostatic stress". Exper. Physiol. (2004) 89(4): 465-471.
Hüttner et al., "Recent advances in the intellectual property landscape of filamentous fungi", Fungal Biol Biotechnol. (2020) 7:16; 17 pgs.
Hyde et al., "The amazing potential of fungi: 50 ways we can exploit fungi industrially". Fungal Diversity (2019) 97(1): 1-136.
Instructables, How to Grow Oyster Mushroom Spawn (Low Tech), retrieved from the internet Aug. 19, 2018: http://www.instructables.com/id/1-How-to-Grow-Oyster-Mushroom-Spawn-Low-Tech/; 17 pages.
Jones et al., "Leather-like material biofabrication using fungi", Nature Sustainability (2020) https://doi.org/10.1038/s41893-020-00606-1, Sep. 7, 2020.
Kamzolkina et al., "Micromorphological features of Pleurotus pulmonarius (Fr.) Quel, and P. ostreaturs (Jacq.) P. Kumm. Strains in pure and binary culture with yeasts". Tsitologiia (2006) 48(2): 153-160.
Kemppainen et al., "Transformation of the Mycorrhizal Fungus Laccaria Bicolor using Agrobacterium tumefaciens." Bioengin Bugs (2011) 2(1): 38-44.
Kerem et al., "Effect of Mananese on Lignin Degradation by Pleurotus ostreatus during Solid-State Fermentation". Applied and Environmental Microbiology (1993) 59(12): 4115-4120.
Kilaru et al., "Investigating dominant selection markers for Coprinopsis cinerea: a carboxin resistance system and re-evaluation of hygromycin and phleomycin resistance vectors". Curr Genet. (2009) 55: 543-550.
Kim et al., "Current Technologies and Related Issues for Mushroom Transformation." Mycobiology (2015) 43(1): 1-8.
Kotlarewski et al., "Mechanical Properties of Papua New Guinea Balsa Wood." European J Wood Wood Products (2016) 74(1): 83-89.
Kück et al., "New tools for the genetic manipulation of filamentous fungi". Appl Microbiol Biotechnol. (2010) 86: 51-62.
Kües, U., "Life History and Development Processes in the Basidiomycete Coprinus Cinereus." Micro Molecular Biol Rev. (2000) 64(2): 316-353.
Kuhar et al., by Ingredi Potassium Sorbate vs Campden Tablets in Wine Making; Jun. 4, 2018. [online]; Retrieved from the Internet <URL: https://ingredi.com/blog/potassium-sorbate-vs-campden-tables-in-wine-making/>; 2 pages.
Kuo, 2005-2006. Glossary of Mycological Terms. Mushroom Expert. Com., pp. 1-13; downloaded from http://www.mushroomexpert.com/glossary.html (May 8, 2015).
Li et al., "Preparation and Characterization of Homogeneous Hydroxyapatite/Chitosan Composite Scaffolds via In-Situ Hydration". J Biomaterials Nanobiotech. (2010) 1: 42-49.

Luo et al., "Coprinus comatus: a basidiomycete fungus forms novel spiny structures and infects nematode." Mycologia (2004) 96(6): 1218-1225.
McPherson et al., "Dissolvable Antibiotic Beads in Treatment of Periprosthetic Joint Infection and Revision Arthroplasty: The Use of Synthetic Pure Calcium Sulfate (Stimulan®) Impregnated with Vancomycin & Tobramycin." Reconstructive Review (2013) 3(1) 12 pages.
Merriam-Webster, "Chamber" dictionary definition; https://www.merriam-webster.com/dictionary accessed Jul. 10, 2017; in 4 Pages.
Merriam-Webster, "pack" Thesaurus definition; https://www.merriam-webster.com/thesaurus; synonyms accessed Aug. 19, 2019; in 10 Pages.
Michielse et al., "Agrobacterium-mediated Transformation of the Filamentous Fungus *Aspergillus awamori*." Nature Protocols (2008) 3(10): 1671-1678.
Mitchell et al., [Eds.] "Solid-State Fermentation Bioreactors." Springer Verlag, Berlin/Heidelberg (2006); TOC in 12 Pages.
Moore D., "Fungal Morphogenesis." Cambridge University Press, Cambridge, UK; (1998) TOC in 8 Pages.
Moore D., "Tolerance of Imprecision in Fungal Morphogenesis." In Proceedings of the 4th Meeting on the Genetics and Cellular Biology of Basidiomycetes (Mar. 1998) pp. 13-19.
Mushroom Growers' Handbook 1, "Oyster Mushroom Cultivation". Part II, Chapter 5, (2005) pp. 75-85.
Mushroom Growers' Handbook 2, "Shiitake Bag Cultivation", Part I Shiitake. Published by Mush World (2005) Chapter 4, pp. 73-90 and pp. 105-109.
Naknean et al., "Factors Affecting Retention and Release of Flavor Compounds in Food Carbohydrates." Inter'l Food Res J. (2010) 17(1): 23-34.
Newaz et al., "Characterization of Balsa Wood Mechanical Properties Required for Continuum Damage Mechanics Analysis." Proceedings of the Institution of Mechanical Engineers, Part L: Journal of Materials: Design and Applications (2016) 230(1): 206-218.
Norvell L., Fungi Biology. Encyclopedia.(2002); 2 pages.
Novoselova et al., "Cocultivation of Pleurotus ostreatus (Jacq.) P. Kumm, with yeasts". Moscow University Biol Sciences Bulletin (2011) 66(3): 102-105.
Nussinovitch "Polymer Macro-and Micro-Gel Beads: Fundamentals and Applications", DOI 10.1007/978-1-4419-6618_2, Springer Science & Business Media LLC (2010) TOC in 8 Pages.
Paz et al., "One Step Contruction of Agrobacterium-Recombination-ready-plasmids (OSCAR): An Efficient and Robust Tool for ATMT Based Gene Deletion Construction in Fungi." Fungal Gen Biol. (2011) 48(7): 677-684.
Peksen et al., "Favourable Culture Conditions for mycelial growth of Hydnum repandum, a medicinal mushroom." African Journal of Traditional, Complementary and Alternative Medicines (2013) 10(6): 431-434.
Peng et al., "Microbial biodegradation of polyaromatic hydrocarbons". FEMS Microbiol Rev. (2008) 32:927-955.
Perez et al., "Myxococcus xanthus induces actinorhodin overproduction and aerial mycelium formation by Streptomyces coelicolor." Microbial Biotech. (2011) 4(2): 175-183.
Philippoussis et al., "Production of Mushrooms Using Agro-Industrial Residues as Substrates", in Biotechnology for Agro-Industrial Residues, Chapter 9, (2009) pp. 163-187.
Poppe J., Mushroom Growers' Handbook 1, 2004, Part II. Chapter 5, "Substrate", pp. 80-81.
Pompei et al., "The Use of Olive Milling Waste-Water for the Culture of Mushrooms on Perlite". Acta Horticulturae (1994) 361:179-185.
Rai et al., "Production of Edible Fungi", in Fungal Biotechnology in Agricultural, Food, and Environmental Applications, D.K. Arora [Ed.], Marcel Dekker, Inc., (2003), Chapter 21, pp. 383-404.
Ross, P., "Pure Culture" 1997-Present; URL: <http://billhoss.phpwebhosting.com/ross/index.php7kind>; downloaded Dec. 14, 2016 in 11 pages.
Royse et al., "Influence of substrate wood-chip particle size on shiitake (*Lentinula edodes*) yield". Bioresource Tehnology (2001) 76(3): 229-233.

(56) References Cited

OTHER PUBLICATIONS

Sapak et al., "Effect of endophytic bacteria on growth and suppression of Tganoderma infection in oil palm". Int J Agric Biol. (2008) 10(2): 127-132.
Schaner et al., "Decellularized Vein as a Potential Scaffold for Vascular Tissue Engineering." J Vascular Surg. (2004) 40(1): 146-153.
Schirp et al., "Production and characterization of natural fiber-reinforced thermoplastic composites using wheat straw modified with the fungus *Pleurotus ostreatus*". J Appl. Polym Sci. (2006) 102:5191-5201.
Scholtmeijer et al., "Effect of introns and AT-rich sequences on expression of the bacterial hygromycin B resistance gene in the basidiomycete Schizophyllum commune". Appl Environ Microbiol. (2001) 67(1): 481-483.
Schuurman J., "Unique agar Pearls." YouTube video; Feb. 16, 2012, <https://www.youtube.com/watch?v=8GqTTOHETPQ>; 1 page.
Science Daily, May 7, 2007, retrieved from the Internet; http://www.sciencedaily.com/releases/2007/05/070506085628.htm., 3 pages.
Seamon K.B., "Forskolin: Unique Diterpene Activator of Adenylate Cyclase in Membranes and in Intact Cells." PNAS (1981) 78(6): 3363-3367.
Sinotech et al., (2015): retrieved from the Internet http://www.sinotech.com/compressionAndTransferMolding.html., 4 pages.
Slater, M. "Young SoRo Entrepreneur Develops Environmentally Friendly Insulation." The Herald of Randolph. Jun. 21, 2007, pp. 1-2.
Staib et al., "Differential expression of the NRG1 repressor controls species-specific regulation of chlamydospore development in Candida albicans and Candida dubliniensis." Molecular Microbiol. (2005) 55(2): 637-652.
Stamets P., "Mycelium Running". Ten Speed Press (2005); pp. 18, 56, 58, 59, 85, 149, 157, 160 and 291 only.
Stamets P., "Growing Gourmet and Medicinal Mushrooms", (Undated) Chapter 21; p. 363.
Stanev et al., "Open Cell Metallic Porous Materials Obtained Through Space Holders. Part I: Production Methods, A Review". JMSE (2016) 139(5): 21 pages.
Stephens et al., "Bringing Cultured Meat to Market: Technical, Socio-political, and Regulatory Challenges in Cellular Agriculture." Trends in Food Science & Technology (2018) 78:155-166.
Sundari et al., "Freeze-drying vegetative mycelium of Laccaria fraterna and its subsequent regeneration". Biotechnology Techniques (1999) 13:491-495.
Tartar et al., "Differential expression of chitin synthase (CHS) and glucan synthase (FKS) genes correlates with the formation of a modified, thinner cell wall in in vivo-produced Beauveria bassiana cells." Mycopathologia (2005) 160(4): 303-314.
Téllez-Jurado et al., "Expression of a heterologous laccase by Aspergillus niger cultured by solid-state and submerged fermentations." Enzyme Microbial Tech. (2006) 38(5): 665-669.
Téllez-Téllez et al., "Growth and laccase production by Pleurotus ostreatus in submerged and solid-state fermentation." Appl Microbiol Biotechnol. (2008) 81(4): 675-679.
Thomas et al., "Growing Orchids in Perlite". In Perlite Plant Guide, The Schundler Company 1951, pp. 1-6, downloaded from http://www.schundler.com/index.html, archived on May 11, 2015.
Timberpress—"How Do Mushrooms Grow So Quickly.", downloaded from the internet: www.timberpress.com/blog/2017/01/how-do-mushrooms-grow-so-quickly, download Feb. 27, 2018 in 7 Pages.
Ugalde U., "Autoregulatory Signals in Mycelial Fungi" in The Mycota: A Comprehensive Treatise on Fungi as Experimental Systems for Basic and Applied Research. K. Esser [Ed.] Springer Publisher, 2nd Edition (2006) Chapter 11; pp. 203-213.
Universal Oil Field, "Sawdust", downloaded from universaloilfield.org on Aug. 23, 2018, 4 pages.
Vara et al., "Cloning and expression of a puromycin N-acetyl transferase gene from Streptomyces alboniger in Streptomyces lividans and *Escherichia coli*". Gene (1985) 33(22): 197-206.

Visser et al., "Pseudoxylaria as stowaway of the fungus-growing termite nest: Interaction asymmetry between Pseudoxylaria, Termitomyces and free-living relatives". Fungal Ecology (2011)4(5): 322-332.
Volk (2003) "Tom Volk's Fungus of the Month for Oct. 1998". This month's fungus is *Pleurotus ostreatus*; the Oyster mushroom, pp. 1-4, downloaded from http://botit.botany.wise.edu/toms_fungi/oct98.html on May 8, 2015.
Wang et al., "Influence of fungal elicitors on biosynthesis of natamycin by Streptomyces natalensis HW-2". Appl Microbiol Biothechnol. (2003) 97: 5527-5534.
Wikipedia, "Water gel (plain)", Wikipedia Contributors downloaded Aug. 21, 2017 in 1 Page.
Wikipedia, "Wood", downloaded on Nov. 26, 2018, 1 page.
Xiao et al., "A Water-soluble Core Material for Manufacturing Hollow Composite Sections." Comp. Structures (2017) 182: 380-390.
Yang et al., "Medicinal Mushroom *Ganoderma lucidum* as a Potent Elicitor in Production of t-Resveratrol and t-Peceatannol in Peanut Calluses". J Agric Food Chem. (2010) 58(17): 9518-9522.
Zadrazil et al., "Influence of $CO_2$ Concentration on the Mycelium Growth of Three *Pleurotus* Species", European J. Appl. Microbiol., vol. 1, pp. 327-335 (1975).
Zimin et al., "The MaSuRCA genome assembler". Bioinformatics (2013) 29(21): 2669-2677.
International Search Report and Written Opinion for PCT/US2019/033601, dated Aug. 6, 2019.
Abbadi et al., "Immunocytochemical identification and localization of lipase in cells of the mycelium of Penicillium cyclopium variety", Appl Microbial Biotechnol (1995) 42: 923-930.
Ando et al., "Cosmetic material for skin whitening—contains mushroom mycelium cultured matter and e.g. ginseng extract, chondroitin sodium sulphate and/or hyaluronic acid", WPI/THOMSON (Jan. 14, 1992), 1992(8): Accession #1992-062018; Abstract of JP4009316A; in 9 pages.
Antinori et al., "Advanced mycelium materials as potential self-growing biomedical scaffolds." Scientific reports (2021) 11(1): 1-14.
Attias et al., "Biofabrication of Nanocellulose-Mycelium Hybrid Materials", Adv Sustainable Syst. (2020) 5(2): 2000196 in 12 pages; Supporting Information in 7 pages.
Borrás et al., "Trametes versicolor pellets production: Low-cost medium and scale-up", Biochem Eng J. (2008) 42(1): 61-66.
Collins English Dictionary, "Cavity", Definition; retrieved on Nov. 8, 2021; 1 page.
Green et al., "Mechanical Properties of Wood", Forest Products Laboratory, 1999. in Wood Handbook—Wood as an engineering material. Gen Tech. Rep. FPL-GTR-113, Chapter 4 in 46 pages.
Hidayat et al., "Characterization of polylactic acid (PLA)/kenaf composite degradation by immobilized mycelia of Pleurotus ostreatus". Inter Biodeter Biodegrad. (2012) 71: 50-54.
Holt et al. "Fungal mycelium and cotton plant materials in the manufacture of biodegradable molded packaging material: Evaluation study of select blends of cotton byproducts." J Biobased Mater Bioenergy (2012) 6(4): 431-439.
Jiang et al., "Manufacturing of Natural Composites with a Mycelium Binder and Vacuum-infused Vegetable Oil-based Resins", Poster dated May 2014; 1 page.
Jiang et al., "Vacuum Infusion of Mycelium-Bound Biocomposite Preforms with Natural Resins", CAMX ExpoConference Proceedings, Oct. 13-16, 2014, 13 pages.
Jiang et al., "Bioresin Infused then Cured Mycelium-based Sandwich-structure Biocomposites: Resin Transfer Molding (RTM) Process, Flexural Properties, and Simulation." J Cleaner Production (2019) 207: 123-135.
Jones et al., "Mycelim Composites: A Review of Engineering Characteristics and Growth Kinetics", J Bionanoscience (2017) 11(4): 241-257.
Jones et al., "Waste-derived Low-cost Mycelium Composite Construction Materials with Improved Fire Safety", FAM (Fire and Materials) (2018) 42(7): 816-825.

(56) References Cited

OTHER PUBLICATIONS

Jones et al., Chitin-chitosan Thin Films from Microbiologically Upcycled Agricultural By-products. In 13th International Conference on the Mechanical Behaviour of Materials, Melbourne, Australia (Jun. 2019) p. 66; in 7 pages.
Kuhn et al., [Eds.] Cell Walls and Membranes in Fungi—An Introduction (Abstract) in Biochemistry of Cell Walls and Membranes in Fungi, Chapter 1, Springer Verlag Berlin/Heidelberg 1990, 2 pages.
Merriam-Webster, "desiccated" (Adj.) Definition; downloaded on Nov. 8, 2021; 1 page.
Meyer et al., "Comparison of the Technical Performance of Leather, Artificial Leather, and Trendy Alternatives." Coatings (Feb. 2021) 11(2): 226; 14 pages.
Pathway-27, "Beta-glucan", Aug. 2012, retrieved from http://http://www.pathway27.eu/topstory/beta-glucan/on Oct. 7, 2021 in 2 pages.
Vetchinkina et al., "Bioreduction of Gold (III) Ions from Hydrogen Tetrachloaurate . . . " Scientific Practical J Health Life Sciences No. 4, ISSN 22188-2268, (2013) pp. 51-56.
Wang et al., "Chemical and structural factors influencing enzymatic saccharification of wood from aspen, birch and spruce". Biomass Bioengin. (2018) 109: 125-134.
Williams, J. "Growth Industry", Financial Times Jan. 12, 2019 (Mogu—Radical by Nature); download from URL <: https://mogu.bio/growth-industry-financial-times-uk-article/> in 1 page.
Wösten et al., "How a fungus escapes the water to grow into the air", Current Biology. (1999) 9(2): 85-88.
Wösten et al., "Growing Fungi Structures in Space", ACT Research Category/Space Architecture; Noordwijk, The Netherlands (Oct. 15, 2018) in 17 pages.
Zeng Z., "Cosmetic composition for cleaning skin, comprises glossy ganoderma spores and collagens, content of glossy ganoderma spores in composition and content of collagens in composition", WPI/Thomson (Feb. 5, 2006) 7: Accession #2007-057767; Abstract of CN1732887A; in 11 pages.
Ziegler et al., "Evaluation of Physico-mechanical Properties of Mycelium Reinforced Green Biocomposites Made from Cellulosic Fibers", Appl Engin Agricult. (2016) 32(6): 931-938.
Bartnicki-Garcia, "Cell wall chemistry, morphogenesis, and taxonomy of fungi", Annual Review Microbiol. (1968) 22(1): 87-108.
Cha et al., "Biomimetic synthesis of ordered silica structures mediated by block copolypeptides". Nature (2000) 403(6767): 289-292.
Dugdale J. "This new surf company is making boards of mushrooms". Blog post—Jun. 25, 2015.
Halseide P., "Cutting brick the safe way". The Aberdeen Group (1988) Publication #M880354 in 2 pages.
Highland Woodworking, "Making Thin Lumber and Veneer Out of Ordinary Boards", Sales Website (2017) in 3 pages.
Holt et al., "Biobased Composition Boards Made from Cotton Gin and Guayule Wastes: Select Physical and Mechanical Properties", Int J Mater Prod Tech. (2009) 36: 104-114.
Islam et al., "Morphology and mechanics of fungal mycelium", Scientific Reports, (2017) 7(1): 1-12.
Kerem et al., "Chemically defined solid-state fermentation of Pleurotus Ostreatus". Enzyme Microbiol Tech. (1993) 15(9): 785-790.
Kokubo et al., "Ca,P-rich layer formed on high-strength bioactive glass-ceramic A-W". J Biomed Mater Res. (1990) 24(3): 331-343.
Koutsoukos et al., "Precipitation of calcium carbonate in aqueous solutions". J Chem Soc., Faraday Trans. 1, Physical Chemistry in Condensed Phases, (1984) 80(5): 1181-1192.
Lu et al., "Theoretical Analysis of Calcium Phosphate precipitation in simulated Body Fluid". Biomaterials (2005) 26(10): 1097-1108—Pre-Pub. Version by Hong Kong University of Science and Technology, Department of Mechanical Engineering, Kowloon; 34 pages.
Molvinger et al., "Porous chitosan-silica hybrid microspheres as a potential catalyst". Chem Mater. (2004) 16(17): 3367-3372.
Monmaturapoj et al., "Influence of preparation method on hydroxyapatite porous scaffolds". Bull Mater Sci. (2011) 34(7): 1733-1737.
Manoli et al., "Crystallization of calcite on chitin". J Cryst Growth, (1997) 182(1-2): 116-124.
Mushroom Source, "Aspen Wood Shavings for Mushroom Cultivation", Website (2015) in 2 pages.
National Institute of Health (NIH/NIBIB), "Tissue Engineering and Regenerative Medicine", Retrieved Sep. 24, 2018 from https://www.nibib.nih.gov/science-education/science-topics/tissue-engineering-and-regenerative-medicine in 13 pages.
Passauer U. et al., "Pilze in Höhlen" [Cave Mushrooms]. Denisia (2016) 37: 211-224.
Stewart B., "Concrete Fence Posts: Fact Sheet", Texas Agriculture Extension Service, Texas A & M University (1975) Article L-1368 in 4 pages.
Trinci et al., "II. Unrestricted Growth of Fungal Mycelia", The Mycota—Growth, Differenciation and Sexuality by Wessels et al. [Eds], Springer, Berlin, Heidelberg, (1994) Chapter II: 175-193.
Udawatte et al., "Solidification of xonotlite fibers with chitosan by hydrothermal hot pressing". J Mater Sci. Lttrs. (2000) 45(6): 298-301.
University of Sydney, "Competition Between Fungi". Webpage, accessed Jul. 16, 2014—http://bugs.bio.usyd.edu.au/learning/resources/Mycology/Ecology/competition.shtml in 3 pages.
Varma et al., "Porous calcium phosphate coating over phosphorylated chitosan film by a biomimetic method". Biomaterials (1999) 20(9): 879-884.
Wagner A. "Mycelium Biking—Eco-Design at its Best", Master's Thesis at Lulea University of Technology (2016) in 92 pages.
Woller R. "The Pearl Oyster Mushroom", University of Wisconsin Website (2011) in 2 pages.
Wan-Mohtar et al., "The morphology of Ganoderma lucidum mycelium in a repeated-batch fermentation for exopolysaccharide production", Biotechnology Reports (2016) 11:2-11.
Weaver et al., "The stomatopod dactyl club: a formidable damage-tolerant biological hammer". Science (2012) 336(6086): 1275-1280.
Yamasaki et al., "A hydrothermal hot-pressing method: Apparatus and Application". J Mater Sci Lttrs. (1986) 5(3): 355-356.
Zivanovic et al., "Changes in Mushroom Texture and Cell Wall Composition Affected by Thermal Processing". J Food Service (2004) 69: 44-49.

* cited by examiner

PROCESS AND APPARATUS FOR PRODUCING MYCELIUM BIOMATERIAL

This application claims the benefit of U.S. Provisional Patent Application 62/675,922, filed May 24, 2018.

This invention relates to a process and apparatus for producing mycelium biomaterials. More particularly, this invention relates to a process and apparatus for producing mycelium biomaterials in static aerated vessels. Still more particularly, this invention relates to a process and apparatus for the production of mycelium biomaterial, and particularly, for the production of fungal biomaterials.

The growth of materials bound together with the mycelium of filamentous fungus is known art, particularly, as described in U.S. Pat. No. 9,485,917.

As is known, fungi operate primarily on oxygen consuming metabolic pathways. Fungi generate carbon dioxide and heat through the same metabolism, both of which can be toxic to further growth of the mycelium. Fungi are limited in the ability to transport oxygen from an area of high availability to a restricted area, due to not having developed respiratory and circulatory transport systems such as are present in animals. Fungi are also limited in their ability to expel build ups of toxic carbon dioxide and heat, again due to a lack of an organism level effective gas or fluid transport mechanism In practice, these limitations mean that grown materials bound by mycelium are limited in their overall volume, based on rates of free diffusion of heat and gases. For simple tray based growth, depths of greater than 6" from an oxygen rich surface are difficult to achieve. Additionally, quantities of material must be separated in such a way as to enable heat removal, such as by filling into 10 lb bags which are spaced apart on racking with air flowing around the grouping of bags, which severely restricts operational efficiency in large scale manufacturing. One successful method of overcoming these limitations in aerobic fermentation methods is to regularly stir the material and fungal colony; however, when the generation of a fully formed bound material is the objective, this method of stirred fermentation is counterproductive.

Accordingly, it is an object of the invention to produce mycelium biomaterials in a relatively simple manner.

It is another object of the invention to be able to grow materials bound by mycelium that are not limited in their overall volume.

It is another object of the invention to provide a process of and apparatus for growing mycelium biomaterials under in non-aseptic open warehouse conditions.

It is another object of the invention to reduce the process cost and complexity of producing mycelium biomaterial.

Briefly, the invention provides a process for producing mycelium biomaterial that provides fresh oxygen to the growing mycelium biomaterial while removing waste heat and waste carbon dioxide by forced aeration through large volumes of material.

The process comprises the steps of mixing a substrate of discrete particles and a fungal inoculum to form a first pourable mixture; and aerating a predetermined height of the mixture in a first phase of fungal expansion for a time and at a temperature sufficient to allow the fungal inoculum to expand and dominate the substrate.

Thereafter, the process comprises the steps of mixing the aerated mixture with added nutrients to form a second pourable mixture; and aerating a predetermined height of the second mixture in a second phase of fungal expansion for a time and at a temperature sufficient to allow the fungal inoculum to bond the discrete particles into a self-supporting biocomposite.

Finally, the process comprises the step of desiccating the biocomposite to form a mycelium biomaterial.

The invention also provides an apparatus for producing mycelium biomaterial. This apparatus includes a blower for generating a steady air stream at a predetermined pressure; an intercooler for regulating the temperature of the air stream; a humidifying unit for humidifying the air stream; a vessel having a cavity for receiving a pourable mixture of discrete particles and a fungal inoculum; and a plurality of nozzles in a base of the vessel in communication with the humidifying unit to deliver humidified air upwardly through the cavity of the vessel and the pourable mixture therein.

The cavity of the vessel may be provided with one or more inserts prior to receiving the pourable mixture so that the inserts may be incorporated in the produced biomaterial.

The cavity of the vessel may be constructed with an internal geometry (void tooling) to make a final product with voids, such as coolers for shipping. A single vessel may incorporate multiple products, such as 48 coolers in one vessel, which would then be cut into final parts after ejection from the vessel.

The invention is a combination of the apparatus required to accomplish aeration as well as the substrate, organism, and process parameters required to successfully achieve controlled reliable growth in the apparatus.

The invention belongs to the category of non-stirred, aerated, solid-state bioreactors, but is unique in the depth of its operation and its ability to operate in a non-aseptic open warehouse conditions, and furthermore in the ability to operate without pasteurization or steam sterilization of the raw materials, dramatically reducing the process cost and complexity. All this is enabled by the specifics of the substrate and process parameters, and in the properties of the materials produced.

Physical System

The apparatus of the invention provides a physical system that consists primarily of an air pre-treatment system and a vessel including air distribution for the production of mycelium biomaterial, and particularly, for the production of fungal biomaterials.

Air Pre-Treatment

Pre-treatment of the air is critical in order to control temperature, humidity, and gas concentrations. Air is introduced to the system through only a coarse particulate filter for protection of the blower 1—high level filtration for asepsis is not required. The blower used is a rotary lobe blower although other styles including compressors, diaphragm pumps, and regenerative blowers could be used. Critically, the blower is capable of providing air at a range or pressure which enables not only passage through the loose substrate prior to growth, but passage through the fully grown material at the end of the process cycle when pressures are highest.

From the blower, the air is cooled to a programmable temperature ($T_1$) by way of the intercooler or fan ventilator. This allows the system to run in an environment with fluctuating external temperatures, and also controls for the variable amount of heat added by the fan, which may change depending on load. Temperature controlled air can then be split into a plurality of flows via a manifold for the support of multiple vessels. Here flow (v/v/m) is also measured to each vessel to ensure that the desired flow rate is achieved.

Programmable air temperature settings, such as cycles where the air temperature drops or raises over time or fluctuates in a cyclical fashion, can be used to drive certain responses from the mycelium. The programmable air temperature settings can also be used to maintain a stable optimal material temperature while the metabolic activity of the mycelium changes over time.

Air at temperature $T_1$ next enters the humidifying unit wherein the air is bubbled through a column of water. The humidifying unit is constructed with sufficient depth and size to provide sufficient moisture into the air to fully saturate the air. Additionally, as the process of evaporating water into the air stream requires heat, a heater may be implemented to add the energy required to continually fully humidify the air, even at very high flow rates. By varying this energy input it is possible to precisely control the humidity level (RH %) in steady state operation. It is noted that the rate of humidification of the air is much more rapid when the temperature of the water ($T_2$) is maintained at or slightly above the temperature of the air ($T_1$). Intentional lowering of the humidity can also be used as a powerful cooling process step.

The humidifying unit (and all parts of the airflow pre-treatment system) must be constructed to handle the pressures which will be sustained at the end of the process, when the material is most completely bound together and has minimum porosity. For this reason, smaller humidification vessels may be used—one for each separate growth vessel—rather than a single much larger humidification vessel which would be costly to build for high pressure operation.

After exiting the humidifying unit, the air is temperature and humidity controlled, and is distributed by insulated hose to the growth vessel.

What has been described is one specific method of generating air with the desired psychrometric properties. It is understood that other methods of temperature control and humidification may be constructed to operate similarly, including but not limited to ultrasonic misting, sling humidifiers, or misting nozzles.

Vessel and Air Distribution

The pre-treated air can be connected to a variety of vessel designs, from custom molded shapes to generic buns for later processing into panels. Construction of the vessel used depends on the nature of the substrate being used, particularly on its porosity, and on other variables such as the metabolic heat generated with the given combination of process parameters.

In its most simple implementation, a single aeration point would be provided at the bottom of a vessel, with air being forced up through the material and exhausting out an open top. As the vessel becomes wider, additional air entry points are needed. In large vessels, an array of nozzles is used, each providing equal flow for generation of uniform materials. It has been found that nozzles which penetrate into the grown material provide better direction of flow and have a greater resistance to side channeling than either a flat bottom with perforations or an air distribution layer (such as loose mulch or gravel).

The nozzles used are specially designed in order to provide uniform back pressure against free flow, therefore maintaining even flow rates through each nozzle and minimizing effects of random porosity variations in the material. In order to maintain this even flow, the pressure drop across the nozzles ($P_{D\_N}$) should be close to or greater than the pressure drop across the loose packed substrate ($P_{D\_S}$). During growth, pressure drop across the substrate will rise by due to the filling in of open gaps in the loose packed substrate with mycelium. Final pressure will equal $P_{D\_N}+P_{D\_S}+P_{D\_G}$ where $P_{D\_G}$ is the added pressure drop due to growth.

The process and apparatus of the invention allows for the processing of grown materials bound by mycelium at depths of greater than 6" and particularly in the range of from 24" to 28".

Substrate

The substrate may be a highly porous material, such as wood shavings, large wood chips, or wood wool, to allow increased air flow and reduce load on the blower.

The substrate may be selected or supplemented to include certain volatile organic compounds, such as terpenes which inhibit contamination. The aeration may be used to prevent the buildup of these compounds in such a way as to select for only certain desirable organisms such as the fungus which was used.

Choice of a suitable primary substrate, comprising the bulk of the raw material, is key in achieving stable and productive operation. Attributes to consider include density, porosity, nutritional availability, phytochemical composition, and cleanliness.

Density of the material primarily affects the final material properties, although density also modifies the back pressure at which "burping", as described herein, occurs. Finally, the bulk substrate compressive resistance must be capable of supporting the material density, such that the vessel depth can be achieved without producing an undesirable density gradient from bottom to top of the vessel.

The porosity of the bulk substrate affects the ease of aeration and therefore the size and power of aeration equipment required to maintain aeration throughout the growth period. Porosity also affects the burp pressure drop and the tendency of air to side channel up walls—especially in vessels with a large height to area ratio such as tall cylinder reactors. Porosity is reflected in the loose substrate pressure drop. The porosity also has biological and material property attributes. A more porous material may require more aerial hyphal growth in order to form strongly interconnected particle bonds, and may produce very different acoustic or mechanical properties than a low porous substrate with small gaps between adjacent particles.

The nutritional availability of the substrate is an absolutely critical attribute in proper design and operation of the system. Nutritional availability must be considered both from the perspective of availability to the desired fungal organism or host of organisms, and also from the perspective of availability to commonly present competitive organisms including bacteria and other fungi.

Nutritional availability to the desired organisms should be balanced to produce growth while not being so readily available that the desired organisms overcome the ability of the aeration system to provide replacement oxygen and remove waste carbon dioxide and heat. In this way, an optimized system may actually restrict nutritional availability to the desired organisms as a means of reducing the volume of air flow required or reducing the ultimate delta T between the bottom and top of the vessel (a function of both fluid flow and heat generation rate).

Nutritional availability to non-desirable organisms (contaminants) should be minimized. A substrate which is highly available to a wide array of organisms (such as a substrate high in simple sugars) will require highly aseptic operation, intensive sterilization, and treatment of the air stream to avoid introduction of any contaminants which will compete with and often overtake the desired organisms. Many models for existing mushroom cultivation and other forms of fermentation use widely accessible substrates requiring exclusion of contaminants through other means, or sequences of composting in order to provide biological exclusion. Ideal operation of the invention herein described involves a substrate which is specifically selected to be nutritionally available to as few possible contaminants as can be managed.

Phytochemical composition of the substrate is similarly important as a way to provide selective pressure for the growth of the desired organism and avoidance of contaminants.

Cleanliness of the substrate is a final consideration in the ideal operation of the process. The cleaner the source, the lower the incoming bioburden load which must be overcome by either pre-processing sterilization or by the desired organism during growth. Cleanliness can be affected by the processing methods and storage methods prior to use.

Given all of the above considerations, the current state of the art substrate for the invention is an Aspen microchip produced from Aspen logs using a modified whole tree drum chipper. The chips are 3 mm×3 mm×1 mm in size. Aspen wood is composed of lignocellulose which is well known to be a highly recalcitrant organic molecule, difficult for most organisms to digest.

Additionally, the optimal substrate for the first phase of biomass expansion may be meaningfully different from what can be used for successive phases of further expansion. Once a certain dominance over the substrate has been achieved by the desired organism, additional amounts of more generally available nutrition (Nut %) may be added. These nutrients are quickly dominated by the population of the desirable organism, which outcompetes possible contaminants that would have out competed a less robust population. In this manner, higher metabolic rate growth and rapid development of mycelium can occur. This initial starving of nutrients followed by nutrient addition is described as phase I ($T_{phaseI}$) and phase II ($T_{phaseII}$) growth.

Organism

The choice of organism involves several considerations including inoculation rate, digestive toolkit, growth temperature dependence, and filamentous cellular morphology.

Inoculation rate (In %) can affect the operation of the described process in several ways. Higher inoculation can be a means of outcompeting contaminants on a more generally available substrate, of increasing final properties or decreasing growth phases. Lower inoculation most simply saves money but can also be a tool to reduce the metabolic rate and therefore lower the aeration requirements and ultimate delta T between the top and bottom of the vessel.

In concert with careful substrate selection, the desired organism should be selected to be capable of digesting and thriving on a nutrient source which is not generally commonly accessible. This combined restriction allows the system in general to be operated with far less aseptic control than is common in the prior art, allowing open air mixing and no filtration.

The organism selected must also be able to grow at a range of temperatures, and with generally similar growth at the range of temperature between $T_{bot}$ and $T_{top}$. Selection for this criterion enables a uniform product.

Lastly, the organism must demonstrate the filamentous properties desired for both operation and final product. If the organism generates too much aerial biomass or exudates, the organism might clog the substrate and increase the pressure drop above the burp pressure or above an economically reasonable pressure for operation. Conversely, if the organism does not generate a sufficiently aerial tissue structure, the particles will not be cohesively bound, and material properties will suffer. The relationship between the pressure drop as a result of growth ($P_{D\_G}$) and the mechanical properties is complicated. This relationship can depend on many attributes, such as the individual cell size and strength, the degree of branching between cells, and the adhesion strength of the cells to the substrate. By organism selection and other process parameter control (such as air flow volume and temperature), it is possible to maximize mechanical properties while not producing an excessive pressure drop. The organism used in the herein described process is a white rot fungus, such as *Ganoderma lucidum* or *Trametes versicolor*.

Operating Parameters

| Parameters | Unit | Specific Example | Range |
|---|---|---|---|
| $T_1$ (cooled air temp) | ° F. | 65 | 45-130 |
| $T_2$ (humidified air/water temp) | ° F. | 70 | 45-130 |
| vvm (air volume per vessel volume per min) | v/v/m | Phase 1 = 0.50 | 0-3 |
| | | Phase 2 = 1.25 | |
| v (air velocity through material) | Ft/min | Phase 1 = 1.2 | 0-7 |
| | | Phase 2 = 2.9 | |
| RH % | % | 100 | 0-100 |
| $P_{D\_N}$ (pressure drop across nozzles) | In H2O | 2-4 | 0.1-30 |
| $P_{D\_S}$ (pressure drop of loose substrate) | In H2O | 1-6 | 0.1-20 |
| $P_{D\_G}$ (additional pressure drop from growth) | In H2O | 12-40 | 12-80 |
| $P_{burp}$ (pressure drop at burp) | In H2O | 13 | |
| $T_{top}$ (temperature at vessel bottom) | ° F. | 70 | 40-110 |
| $T_{bot}$ (temperature at vessel top) | ° F. | 90 | 41-110 |
| H (vessel height) | Inches | 28 | 12-72 |
| L (vessel width) | Inches | 39 | 24-192 |
| W (vessel length) | Inches | 39 | 24-4,800 |
| In % (wet inoculation % by dry substrate) | % | 10 | 0.5-20 |
| Nut % (nutrient % by dry substrate) | % | 7 | 3-20 |
| $T_{phaseI}$ (duration of phase I) | Days | 5 | 2-7 |
| $T_{phaseII}$ (duration of phase II) | Days | 4 | 1-5 |

Product

The final product may take a variety of forms, including but not limited to a block, flat panels, or a molded shape.

In the case of a block, the vessel would be rectangular and produce a rectangular block or bun. In this instance, humidification might be turned off and air temperature raised while the block is still in the reactor, initiating a drying phase which kills the fungus and stabilizes the material (avoiding the overheating which could occur from removing a biologically active block from the cooling air). Such blocks might be used for civil engineering, or as blanks for carving into architectural components.

In the case of panels, a block (either pre-dried while in the vessel or still fully biologically active) would be removed from the vessel and sliced into a multiplicity of panels. This can be achieved using commonly available sawmill equipment. Panels from 0.25" up to the full thickness of the block can be produced. Slicing of the block into thin panels allows faster low energy drying and heat treatment than thicker panels. Alternatively, after cutting and before drying, panels can be further incubated to provide surface growth and further strengthening, or to be grown together into larger three dimensional objects.

Potential applications of panels produced in this method include furniture surface and door cores, acoustic panels, insulation panels, rafts for wetland remediation, components for set design, temporary sign panels, and flat sheet packaging material.

The vessel may also be formed as a molded volume for the production of useful shapes, such as a chair or couch substructure or a plurality of shipping cooler volumes. In the case of a chair substructure, additional strengthening and attachment components, such as pieces of wood, may be placed into the vessel prior to filling, and allowed to grow into place. As with the block, some amount of drying while in the vessel can be used to shorten drying time. In the case of shipping coolers, a number of parts might be grown together in a single molded vessel, and then cut apart into individual units for commercial sale either before or after drying.

Modifications

The mixture may be grown only in phase 1 in the vessel, and then moved into a different vessel for phase 2, after being mixed with nutrients.

The second vessel may be a non-aerated mold or a multiplicity of non-aerated molds, such as a series of thermoformed plastic trays with dimensions of 21"×21". These molds may be open on top and may include several depressions for filling with the mixture to form shapes, such as, corner blocks for packaging.

The mixture may be grown only in phase 1 in the vessel, and then moved into a different vessel after being mixed with nutrients and not subjected to a phase 2. In this case, after being mixed with nutrients, the mixture is incubated for a time sufficient to allow said fungal inoculum to bond said discrete particles into a self-supporting biocomposite, such as described in U.S. Pat. No. 9,485,917.

The second vessel may also be shaped earth outdoors, for example the bottom of a ditch or depression being prepared for a stream or pond, and where the material will grow in place during a non-aerated phase 2 (at depths <12 inches). The final grown layer may act as an impermeable layer or a load bearing surface, such as a temporary road.

The vessel may take the form of a stationary lane or tunnel where the material is mixed in-vessel between phase 1 and phase 2 and then unloaded by drag conveyor or hoist.

These and other objects and advantages will become more apparent from the following detailed description taken with the accompanying drawings wherein:

FIG. 1 schematically illustrates the process steps of the invention;

FIG. 2 graphically illustrates the parameter selection, process feedback loop and product attributes for the process of the invention;

FIG. 3 schematically illustrates an apparatus in accordance with the invention;

DETAILED DESCRIPTION

Figure 1:
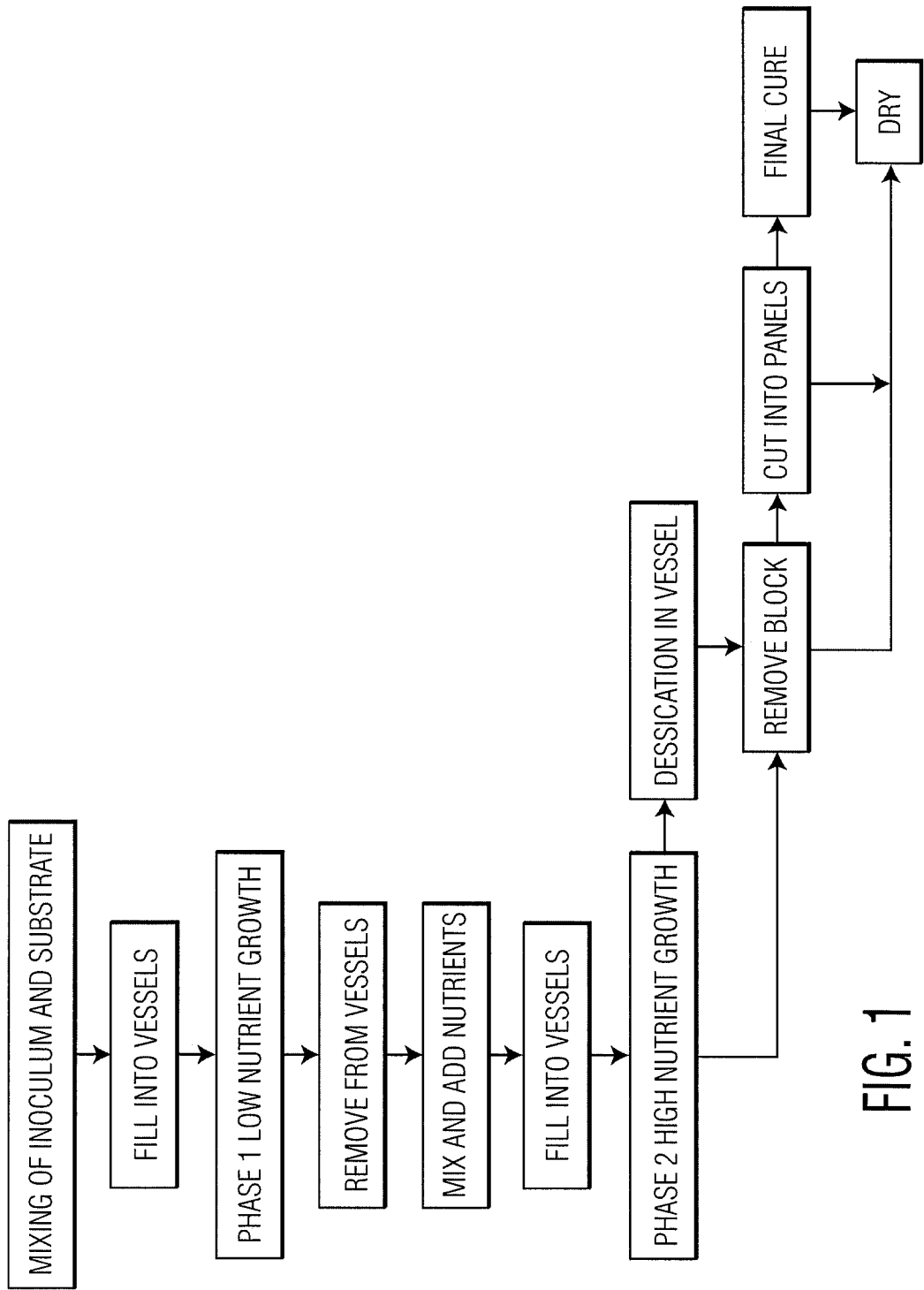

Referring to FIG. 1, a process for the production of fungal biomaterials includes a step of mixing inoculum, e.g. *Ganoderma Lucidum* or *Trametes* sp. in an amount of 1-10% by dry mass, and a substrate of discrete particles e.g. Aspen chips to form a pourable mixture. The mixture may be mixed in a continuous screw mixer or batch ribbon blender, and the Aspen chips may be exposed to sterilization e.g. atmospheric steam prior to being chilled and mixed with the inoculum.

The process also includes a step of dispensing the mixture into one or more vessels. The vessels may be bins having dimensions of 40"×40"×28" and are filled to a height of 24"-28". The mixture may be compacted into a vessel as the vessel is filled.

Thereafter, the mixtures in the vessels are subjected to a step of aeration for a time and at a temperature sufficient to allow the fungal inoculum to expand and dominate the substrate. This step provides a Phase I low nutrient growth. During this step, aeration may be low, e.g. 0.50 v/v/m, since there is little readily available nutrition and thus relatively little heat generation. During this step, the fungal portion of the mixture is able to outcompete any contaminant organisms and expand to cover and dominate the wood chip portion of the mixture. The end result of this step is that the mixture is evenly coated in the fungal tissue; however, it is still easy to break apart and remix.

Next, the mixture is removed from the vessel(s) and mixed with added nutrients.

The mixture with the added nutrients is then poured into a second vessel having a cavity of the final desired shape for the product. Alternatively, the mixture with the added nutrients may be poured back into the first vessel, if that vessel has a cavity of the final desired shape for the product. One advantage of using two vessels is that the vessels can be used in rotation for faster operation.

The addition of nutrients is performed after the fungus has established dominance and is able to outcompete any potential contaminant organisms for access to the easily digestible additional nutrients.

These nutrients are quickly converted into additional fungal tissue biomass, which binds the mixture into its final form. The mixture is then subjected to Phase II aeration, which is higher in velocity and potentially cooler to combat the additional metabolic energy generated by the added nutrients.

During the Phase II aeration, the biomass is aerated for a time and at a temperature sufficient to allow the fungal inoculum to bond the discrete particles into a self-supporting biocomposite.

After solidifying in its final shape, the biocomposite is either desiccated in the vessel or ejected from the vessel while still wet and then dried.

The ejected wet biocomposite may be either dried and further processed, or further processed and then dried. Further processing may include being machined into smaller components such as 1" panels.

Sheets of the wet biocomposite may be further processed by either a final incubation stage at 100% humidity and 80° F. to form a layer of tissue on the cut surfaces, or by being assembled into a final shape such as a box and being incubated in the same conditions in order to grow together.

Flexible sheets cut from a block may also be pressed into 3D contours by a heated press at 400° F. in a combination drying and forming step.

Final drying of the biocomposite can occur at ambient temperatures over the course of a week or more, or can be expedited to as fast as 24 hours at 180° F. in a wood kiln style dryer. Blocks or panels left covered outdoors for several weeks in a climate with temperatures between 40° F. and 90° F. will continue to harden, producing an aged material.

Figure 2:
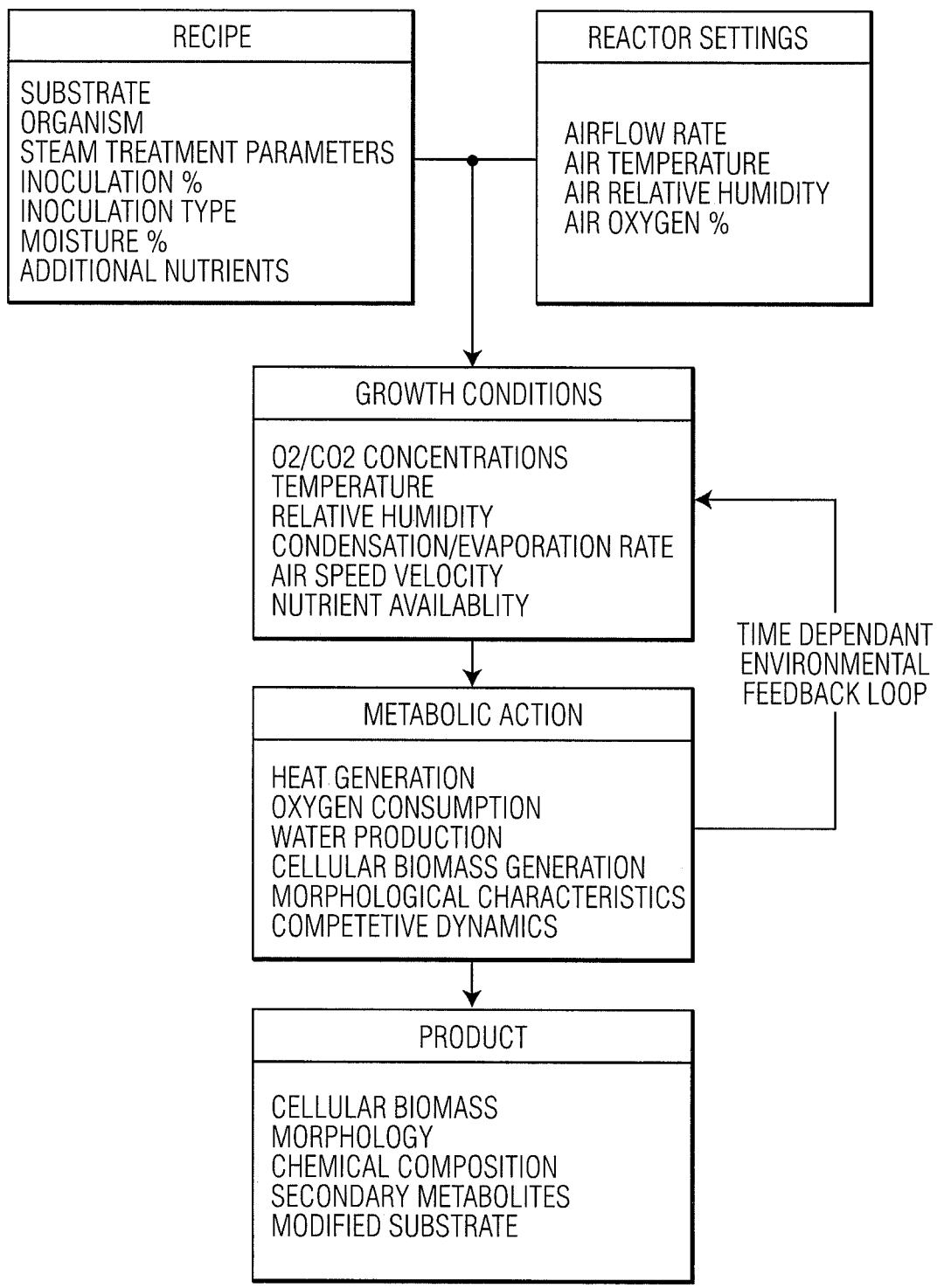

Referring to FIG. 2, the production of mycelium biomaterial in a static aerated vessel requires the selection of a recipe and of reactor settings. Recipe selection includes selection of substrate, organism, steam treatment parameters, inoculation %, inoculation type, moisture %, and additional nutrients. A given recipe might be aspen planer shavings, *G. lucidum*, with or without atmospheric steam treatment for 10 minutes, a 5% by dry mass inoculation rate, a synthetic fine inoculation type, a moisture percentage of 65%, and additional nutrients of second clear flour.

Reactor settings include the air flow rate, the air temperature, the air relativity, and the oxygen percentage. A given recipe might be 0.5 v/v/m for phase I and 1.25 v/v/m for phase II, an air temperature of 75° F., a relative humidity of 100%, and an oxygen percentage equal to atmospheric concentrations.

As further illustrated in FIG. 2, the recipe and reactor settings result in conditions within the vessel which can be characterized as the growth conditions. These conditions include the $O_2$ and $CO_2$ concentrations, the temperature, the relative humidity, the rate of evaporation of moisture, the air speed velocity, and the nutrient availability. An example is an $O_2$ concentration greater than 5%, a temperature less than 95° F. throughout the vessel, an evaporation rate at <2% of moisture content per day, an airspeed velocity of 1.2 ft/min in phase I and 2.9 ft/min in phase II, and a recalcitrant nutrient availability in phase I and a simple starch nutrient availability in phase II.

As further illustrated in FIG. 2, the growth conditions dictate the metabolic action which occurs in the fungal tissue. This includes the heat generation, the oxygen consumption rate, the water production rate, the cellular biomass generation rate, the specific morphological characteristics, and the competition dynamics. As an example, the metabolic action may consist of heat generation of 1 Watt per wet pound of mixture, Oxygen consumption low enough to be replaced by the fresh air stream, water production sufficient to maintain the <2% moisture content loss per day rate, cellular biomass generation rate of 1% of dry mixture weight per day, morphological characteristics for maximum strength such as a high quantity of highly cross-linked and branched cells, and a strong dominance over establishment of competitive organisms.

As further illustrated in FIG. 2, the metabolic action at any given point in time may modify the growth conditions within the reactor, which in turn dictate the metabolic conditions. This may result in time dependent changes such as a slow increase in temperature. Reactor settings may also be modulated through time to effect results such as a slow decrease in temperature or increase in aeration.

Lastly, as shown in FIG. 2, the final material properties are a result of the metabolic activity. These properties include the cellular biomass, the morphology, the chemical composition, secondary metabolites, and modification of substrate. An example process may result in a cellular biomass of 5% by dry mass mixture, a morphology of highly branched vegetative cells, a chemical composition favoring strong cell walls, expression of secondary metabolites for increased hydrophobicity, and modification of the chemistry of the substrate to make more accessible for animal feed.

Figure 3:
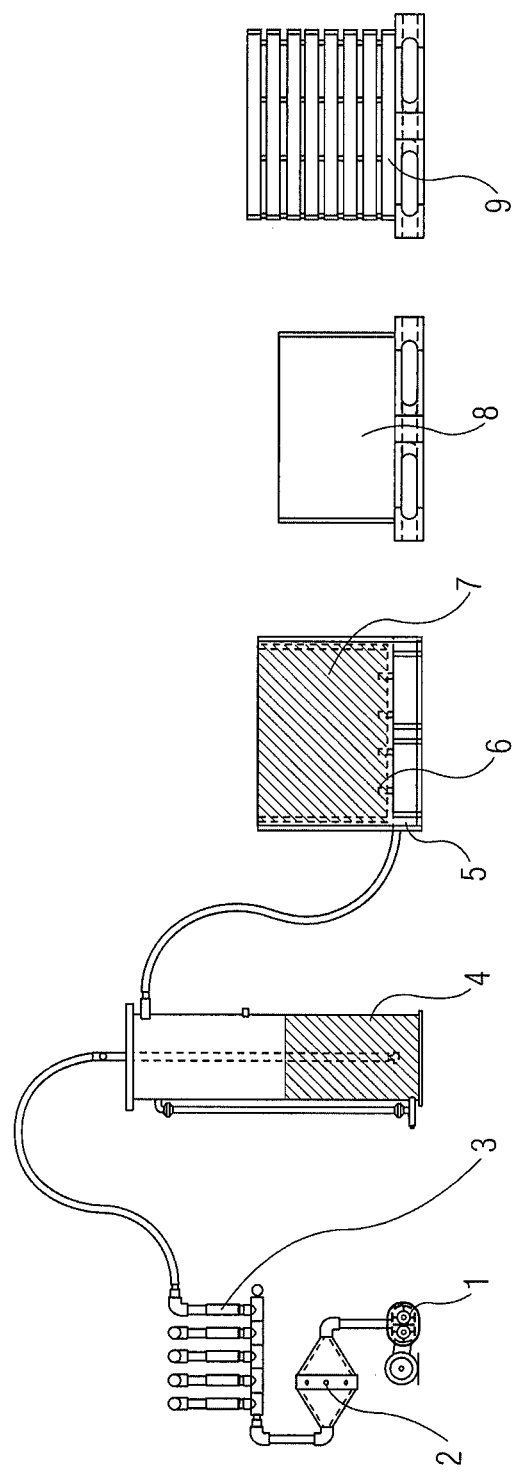

Referring to FIG. 3, an apparatus for the production of fungal biomaterials includes a blower 1, an intercooler 2, a manifold 3, a humidifying unit 4, a vessel 5 and a plurality of air flow nozzles 6 in the base of the vessel 5.

The blower 1 operates to provide a steady air stream at sufficient pressure to flow through the vessel 5, even after tissue growth has occurred.

The intercooler 2 operates to regulate the air temperature out of the blower 1 and to remove heat introduced due to compression.

The manifold 3 operates to separate a pressurized temperature controlled airflow into multiple vessels and includes a means of regulating and measuring the flow to each vessel independently.

The humidifying unit 4 operates as a final temperature control tank for the purpose of raising the humidity of the air stream up to full saturation as well as entraining water mist into the air stream for an additional supply of moisture to the vessel 5. A heater (not shown) is included for the purpose of replacing the heat of vaporization removed by the evaporation of water.

The airflow nozzles 6 operate to distribute the temperature and humidity controlled air stream evenly into the vessel 5 and for the purpose of injecting the air into the growing material 7 in the vessel 5 to prevent side channeling and provide even aeration to all parts of the mixture.

The apparatus serves to produce a finished block of grown material 8 that is ejected from the vessel 5 and subsequently sliced into panels 9. As indicated, the panels 9 may be stacked in vertically spaced apart manner for the purpose of either final curing or more efficient drying by convection.

Figure 4:
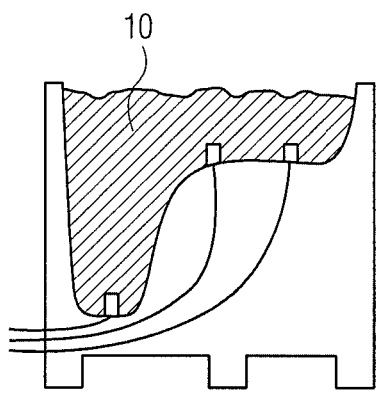
FIG. 4 illustrates a partial cross-sectional side view of a vessel employed in the apparatus of the invention.
Figure 5:
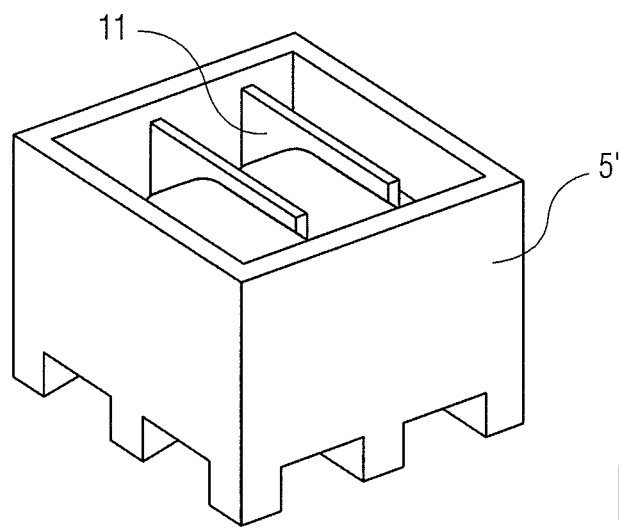
FIG. 5 illustrates a vessel provided with inserts in accordance with the invention.
Figure 6:
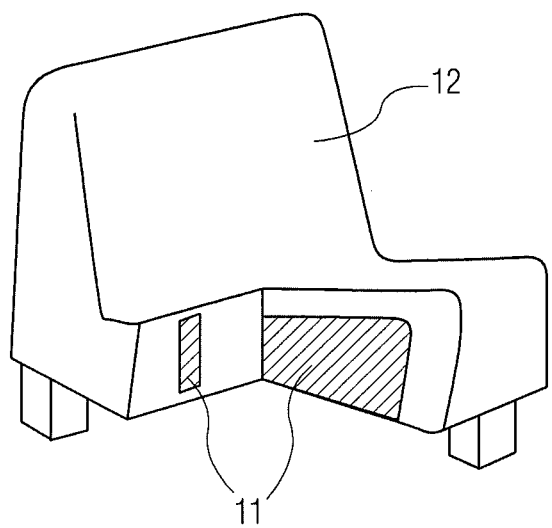
FIG. 6 illustrates a view of a produced mycelium biomaterial with a pair of inserts incorporated therein in accordance with the invention.

Referring to FIGS. 4, 5 and 6, for Phase II, the aeration vessel 5' may be constructed with a cavity 10 of a geometry to make a final product 12, such as a chair or sofa (FIG. 6).

In addition, the cavity 10 of the vessel 5' may be provided with one or more inserts 11 (FIG. 5) prior to receiving the pourable mixture for Phase II so that the inserts 11 may be incorporated in the produced biomaterial product, providing additional benefit, such as wood support beams or tack strips for upholstery.

Referring to FIG. 7 to 10, wherein like reference characters indicate like parts as above, the vessel 5' may be constructed with an internal geometry (void tooling) to make a final product with voids, such as coolers for shipping. A single vessel 5' may incorporate multiple products, such as 48 coolers in one vessel, which would then be cut into final parts after ejection from the vessel.

Figure 7:
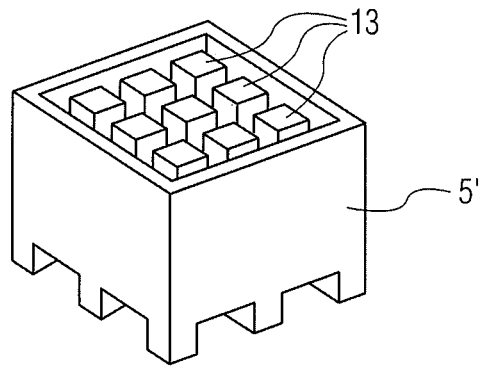
FIG. 7 illustrates a vessel constructed with an internal geometry to make a final product with voids.
Figure 8:
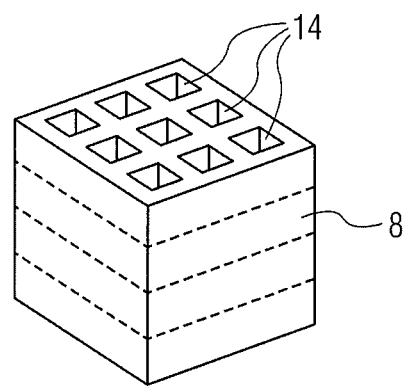
FIG. 8 illustrates a multi-cavity block made in accordance with the process of the invention.

As illustrated in FIG. 7, the vessel 5' is provided internally with a plurality of upstanding posts 13 in order to produce a single block of grown material 8, i.e. of mycelium biomaterial, as shown in FIG. 8 with a plurality of longitudinally extending tunnels 14 corresponding in cross-sectional shape to the cross-sectional shape of the posts 13 in the vessel 5'.

Figure 9:
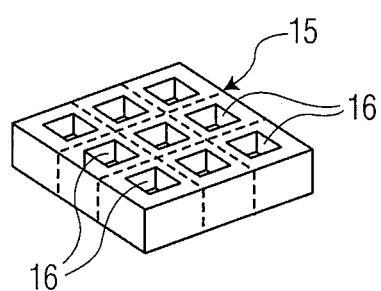
FIG. 9 illustrates a layer cut from the block of FIG. 8.

Referring to FIG. 9, the block 8 of FIG. 8 may be cut transversely into a plurality of layers 15, only one of which is illustrated. As indicated, the layer 15 contains a plurality of openings 16 corresponding to the pattern of posts 13 in the vessel 5'.

Figure 10:
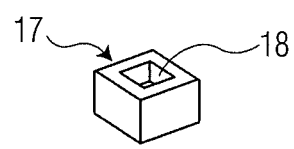
FIG. 10 illustrates a segment separated from the layer of FIG. 9.

Referring to FIG. 10, the layer 15 of FIG. 9 may be cut into individual segments 17, only one of which is shown, with a single aperture 18.

Figure 11:
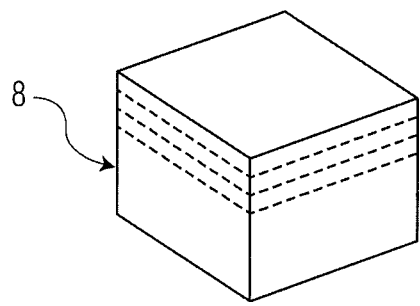
FIG. 11 illustrates a large block of fungal biomaterial made in accordance with the process of the invention.
Figure 12:
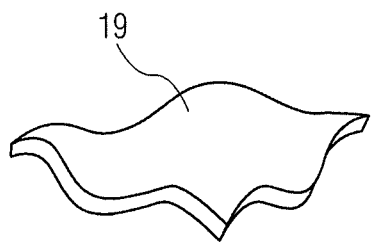
FIG. 12 illustrates a thin sheet cut from the block of FIG. 11.

Referring to FIGS. 11 and 12, wherein like reference characters indicate like parts as above, a block of grown material 8 may be cut into a plurality of flat sheets or panels 19, only one of which is illustrated.

Figure 13:
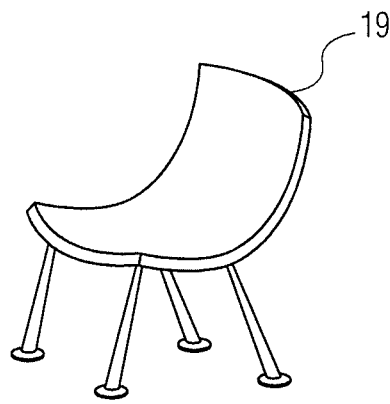
FIG. 13 illustrates a thin sheet from the block of FIG. 11 in place as a landscape mat.
Figure 14:
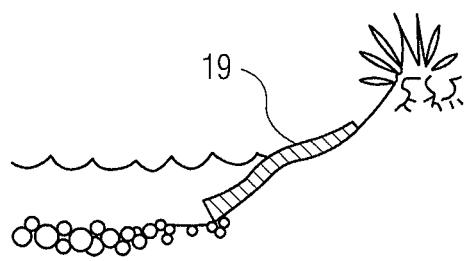
FIG. 14 illustrates a sheet from the block of FIG. 11 in place as a seat for a chair.

The flat panels 19 may be cut thin enough for the final product to be flexible for use in products, such as conformable landscape mats (FIG. 13) to prevent erosion and weed growth. The flat panels 19 may also be used in products, such as molded chair backs (FIG. 14) where the thin panels might be compression molded into complex three dimensional geometries.

A plurality of flat panels 19 may also be assembled into a final shape (not shown) and finish grown to make a final product such as coolers for shipping.

Figure 15:
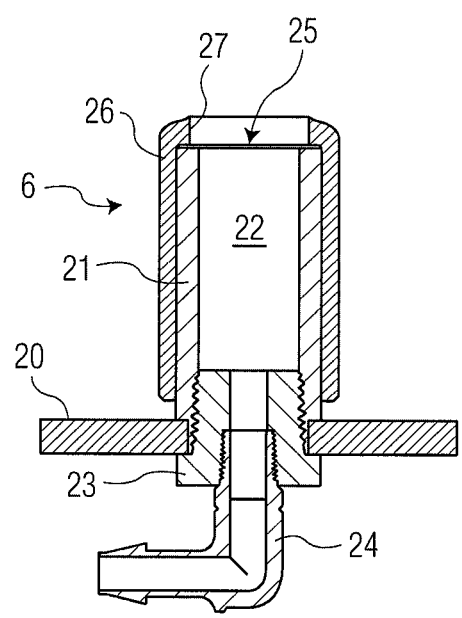
FIG. 15 illustrates a cross-sectional view of a nozzle employed in the apparatus of the invention.

Referring to FIG. 15, each nozzle 6 is mounted in the base 20 of a vessel and includes a cylindrical body 21 disposed within the vessel to define an expansion chamber 22 and a nut 23 threaded into the cylindrical body 21 from outside the base 20 of the vessel to secure the cylindrical body 21 to the base 20. In addition, each nozzle 6 includes a connecting piece 24 secured in the nut 23 to deliver a restricted flow of air from the humidifying unit 4 (see FIG. 3) through the nut 23 and into the expansion chamber 22. The connecting piece 24 serves as a flow restriction area which provides back pressure.

Also, a mesh screen 25 is disposed on the cylindrical body 21 over the expansion chamber 22 and a cylindrical cover 26 is slidably mounted over the cylindrical body 21 and the mesh screen 25. The cover 26 has an opening 27 coaxial with the expansion chamber 22 to deliver air therethrough.

The cross sectional areas of the screen 25 and expansion chamber 22 are selected such that even with partial blockage due to substrate chips lying against the screen 25, the remaining cross sectional area is still greater than the cross sectional area of the flow restriction area. This minimizes flow variation between nozzles due to the random orientation of chips on the screens. Without this feature, one nozzle might be blocked by chips while another might have free flowing air. Additionally, each nozzle 5 extends into the material to decrease air channeling across the vessel wall.

It is important to note here that if $P_{D\_S}+P_{D\_G}$ exceeds force of gravity on the substrate, the growing material will lift, opening low resistance air-flow channels that will bypass the material and reduce aeration effectiveness. This is colloquially termed "burping" and whether it occurs in operation is a combined function of the porosity of the substrate, the density of tissue growth, the air flow rate required, and the density of substrate—which all combine to dictate the burping back pressure ($P_{burp}$).

One critical dimension is the height (h) of the vessel 5 (FIG. 3). If aeration is introduced on a single side, for example on the bottom of a rectangular open top vessel, and if the vessel is sufficiently large in the length and width dimensions that heat loss through the walls cannot be considered for the central material, then in the core it is essentially a one dimensional thermodynamic and fluid dynamic system. In such a system, with heat being generated by each successive unit layer of material, the delta between the temperature of the material at the bottom of the vessel ($T_{bot}$) and at the top ($T_{top}$) will be directly related to the height of the vessel.

By the same reasoning, there will always be a temperature difference between the bottom and top of the vessel, so long as the material is generating heat and being cooled by aeration. It is important that the air flow rate, the metabolic conditions, the energy availability of the substrate, the organism selected for growth, and the height of the vessel all be selected in concert in order to provide that the delta T between top and bottom is small enough that final properties compared from the top and bottom of the material are both within desired specifications.

The final parameter for the vessel is the top surface treatment. Aeration can be used as a means to reduce the settling of contaminant spores on the material; however, for additional exclusion of surface contamination, a lid may be desired. This lid may take the form of a physical barrier, with features allowing for escape of the aeration air, but such lids can trap condensation, heat, and moisture. As described herein use is made of a permeable top layer of material specifically selected to prohibit the growth of any contamination, such as wood ash. This allows for the free flow of aeration air without formation of condensation or trapping of hot exhaust gases. Once an inhibitory priority effect has been established, the permeable top layer may be removed.

The vessel should be one which can be filled, moved around, and dumped. The same ventilation system may be applied to much larger lanes, as are used in commercial composting. Here, substrate is loaded in, mixed in place when needed, and might be extracted by way of a drag net conveyor, again as is used in composting.

Lanes are vessels which are fixed construction cement structures of substantially large size. A lane would be on the order of 100-400 feet long and 6-10 feet wide vs. a 4'×4' vessel.

Whereas the vessels, such as a 4'×4' vessel, are portable and can be flipped upside-down to extract the product, lanes are not movable, and finished product must be pulled out of the lane. Also, for the mixing step where added nutrients are mixed in, portable vessels are small enough that the contents can be dumped into a mixing machine, and then dispensed back into the small vessel. For lanes, the nutrients are added directly into the lane, and then a piece of mixing equipment (such as an auger on a gantry system) must mix the mixture within the lane.

Thus, the invention provides a process and apparatus for producing mycelium biomaterials in a relatively simple manner and mycelium biomaterials that are not limited in their overall volume.

The invention also provides a process and apparatus for growing mycelium biomaterials under non-aseptic open warehouse conditions thereby reducing the process cost and complexity of producing mycelium biomaterial.

What is claimed is:

1. A process for producing mycelium biomaterial comprising the steps of
mixing a substrate of discrete particles and a fungal inoculum to form a first pourable mixture;
aerating a predetermined height of said mixture in a first phase of fungal expansion for a time and at a temperature sufficient to allow said fungal inoculum to expand and dominate said substrate;
thereafter mixing said aerated mixture with added nutrients to form a second pourable mixture;
aerating a predetermined height of said second mixture in a second phase of fungal expansion for a time and at a temperature sufficient to allow said fungal inoculum to bond said discrete particles into a self-supporting biocomposite; and
thereafter desiccating said biocomposite to form a mycelium biomaterial.

2. The process of claim 1, wherein said fungal inoculum is one of *Ganoderma lucidum* and *Trametes versicolor*.

3. The process of claim 1, wherein said step of aerating said mixture comprises introducing humidified air upwardly into said mixture.

4. The process of claim 3, wherein said step of aerating said second mixture comprises introducing humidified air upwardly into said mixture.

5. The process of claim 4, wherein said second mixture is aerated at a higher velocity than said first mixture.

6. The process of claim 1, wherein said first phase of fungal expansion occurs in a vessel having a cavity receiving said first mixture.

7. The process of claim 6, wherein said second phase of fungal expansion occurs in said vessel.

8. The process of claim 6, wherein said second phase of fungal expansion occurs in a second vessel having a cavity of predetermined shape whereby said self-supporting biocomposite has a shape conforming to said cavity of said second vessel.

9. The process of claim 8, wherein said self-supporting biocomposite is a blockshaped biocomposite, and wherein said process further comprises the step of cutting said blockshaped biocomposite into sheets.

10. The process of claim 1, further comprising the step of placing a permeable layer of material capable of prohibiting growth of contamination on top of said predetermined height of said second mixture prior to said step of aerating said second mixture in said second phase of fungal expansion.

11. A process for producing mycelium biomaterial comprising the steps of
mixing a substrate of discrete particles and a fungal inoculum to form a first pourable mixture;
dispensing said mixture into a vessel to fill said vessel to a predetermined height within said vessel;
aerating said mixture within said vessel in a first phase of fungal expansion for a time and at a temperature sufficient to allow said fungal inoculum to expand and dominate said substrate;
thereafter mixing said aerated mixture with added nutrients to form a second pourable mixture;
dispensing said second pourable mixture into a second vessel;
aerating said second pourable mixture within said second vessel in a second phase of fungal expansion for a time and at a temperature sufficient to allow said fungal inoculum to bond said discrete particles into a self-supporting biocomposite; and
thereafter desiccating said biocomposite to form a mycelium biomaterial.

12. The process of claim 11, wherein said second vessel has a cavity of predetermined three dimensional shape to receive said second pourable mixture and said biocomposite conforms to said shape.

13. The process of claim 11, further comprising the step of placing inserts into said second vessel prior to said step of dispensing said second mixture into said second vessel to define a plurality of cavities for dispensing of said second pourable mixture thereinto.

14. The process of claim 13, wherein said second pourable mixture in each said cavity of said second vessel is aerated to allow said fungal inoculum to bond said discrete particles into a self-supporting biocomposite in each said cavity.

15. The process of claim 11, further comprising the step of placing a permeable layer of material capable of prohibiting growth of contamination on top of said second pourable mixture in said second vessel prior to said step of aerating said second pourable mixture.

* * * * *